US012799221B2

(12) United States Patent
Bisht et al.

(10) Patent No.: US 12,799,221 B2
(45) **Date of Patent: *Nov. 17, 2026**

(54) CRTAM ANTIBODIES AND METHODS OF TREATING CANCER

(71) Applicant: Oxford BioTherapeutics Ltd, Oxford (GB)

(72) Inventors: Arnima Bisht, San Jose, CA (US); Rachel L. Dusek, San Jose, CA (US); Haining Huang, San Jose, CA (US); Chuck Hannum, San Jose, CA (US); James Edward Ackroyd, Oxford (GB); Livija Deban, Oxford (GB)

(73) Assignee: Oxford BioTherapeutics Ltd, Oxford (GB)

( * ) Notice: Subject to any disclaimer, the term of this patent is extended or adjusted under 35 U.S.C. 154(b) by 7 days.

This patent is subject to a terminal disclaimer.

(21) Appl. No.: 18/140,892

(22) Filed: Apr. 28, 2023

(65) Prior Publication Data

US 2024/0132614 A1 Apr. 25, 2024
US 2024/0228649 A9 Jul. 11, 2024

Related U.S. Application Data

(63) Continuation of application No. 16/760,180, filed as application No. PCT/GB2018/053165 on Nov. 1, 2018, now Pat. No. 11,673,963.

(Continued)

(51) Int. Cl.
*A61K 39/395* (2006.01)
*A61P 35/00* (2006.01)
(Continued)

(52) U.S. Cl.
CPC ...... *C07K 16/2896* (2013.01); *A61K 39/3955* (2013.01); *A61P 35/00* (2018.01);
(Continued)

(58) Field of Classification Search
None
See application file for complete search history.

(56) References Cited

U.S. PATENT DOCUMENTS 9,550,825 B2 * 1/2017 Takada .................... A61P 25/04
2015/0361164 A1 12/2015 Takada et al.
(Continued)

FOREIGN PATENT DOCUMENTS

EP 2949675 A1 12/2015
WO 2005/012530 A2 2/2005
(Continued)

OTHER PUBLICATIONS

Herold et al., Determinants of the assembly and function of antibody variable domains, Scientific Reports, 7:12276, DOI:10.1038/s41598-017-12519-9, 17 pages, Sep. 2017.*
(Continued)

*Primary Examiner* — Claire Kaufman
(74) *Attorney, Agent, or Firm* — Nelson Mullins Riley & Scarborough LLP; Jane E. Remillard, Esq.; Jill Gorny Sloper, Esq.

(57) ABSTRACT

Disclosed herein are antibodies directed against CRTAM, nucleic acids encoding such antibodies, host cells comprising such nucleic acids encoding the antibody, methods for preparing anti-CRTAM antibodies, and methods for the treatment of diseases, e.g., human cancers, including but not limited to small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gall-
(Continued)

bladder and bile ducts, uterine, adrenal cancers, sarcomas, GIST, neuroendocrine tumours, and haematological malignancies.

12 Claims, 7 Drawing Sheets

Specification includes a Sequence Listing.

Related U.S. Application Data

(60) Provisional application No. 62/697,145, filed on Jul. 12, 2018, provisional application No. 62/580,667, filed on Nov. 2, 2017.

(51) Int. Cl.
*C07K 16/28* (2006.01)
*A61K 39/00* (2006.01)

(52) U.S. Cl.
CPC .... *A61K 2039/505* (2013.01); *C07K 2317/24* (2013.01); *C07K 2317/31* (2013.01); *C07K 2317/33* (2013.01); *C07K 2317/565* (2013.01); *C07K 2317/73* (2013.01)

(56) References Cited

U.S. PATENT DOCUMENTS

| | | | |
|---|---|---|---|
| 2017/0022286 | A1 | 1/2017 | Kohrt |
| 2020/0262927 | A1 | 8/2020 | Bisht et al. |

FOREIGN PATENT DOCUMENTS

| | | | |
|---|---|---|---|
| WO | 2009/029883 | A2 | 3/2009 |
| WO | 2014115430 | A1 | 7/2014 |
| WO | 2015009726 | A2 | 1/2015 |
| WO | 2016/154341 | A1 | 9/2016 |

OTHER PUBLICATIONS

Mimoto et al., Engineered antibody Fc variant with selectively enhanced FcgRIIb binding over both FcgRIIaR131 and FcgRIIaH131, Prot. Eng. Design Select. 26(10:589=598, 2013.*

Andria, M. et al., "Diverse VH and VL genes are used to produce antibodies against a defined protein epitope," J. Immunol. 144(7):2613-2619 (1990).

Arase, N. et al., "Heterotypic interaction of CRTAM with Necl2 induces cell adhesion on activated NK cells and CD8 (+) T cells," International Immunology, vol. 17(9):1227-1237 (2005).

Boles, K. et al.,"The tumor suppressor TSLC1/NECL-2 triggers NK-cell and CD8(+) T-cell responses through the ceff-surface receptor CRTAM," Blood, vol. 106(3):779-786 (2005).

Chen, C. et al., "Enhancement and destruction of antibody function by somatic mutation: unequal occurrence is controlled by V gene combinatorial associations," EMBO J., vol. 14(12):2784-2794 (1995).

Fadeel, B. et al., "Anti-Fas IgG1 antibodies recognizing the same epitope of Fas/APO-1 mediate different biological effects in vitro," Intl. Immunol., vol. 9(2):201-209 (1997).

Galibert L. et al., "Nectin-like protein 2 defines a subset of T-cell zone dendritic cells and is a ligand for class-I- restricted T-cell-associated molecule," J. Biol Chem, vol. 280(23):21955-2196 (2005).

International Preliminary Report on Patentability, PCT/GB2018/053165, dated May 5, 2020, 8 pages.

International Search Report and Written Opinion, PCT/GB2018/053165, dated Jan. 3, 2019, 13 pages.

Kim, H-R. et al., "IGSF4 is a novel TCR [zeta]-chain-interacting protein that enhances TCR-mediated signaling," The Journal of Experimental Medicine, vol. 208 (12):2545-2560 (2011).

Ladner, R.C., "Mapping the epitopes of antibodies," Biotechnol. Genet. Eng. Rev., vol. 24:1-30 (2007).

Lamminmaki, U. et al., "Chrystal structure of a recombinant anti-estradiol Fab fragment in complex with the 17beta-estradiol," J. Biol. Chem., vol. 276(39):36687-94 (2001).

MacCallum, R. et al., "Antibody-antigen interactions: contact analysis and binding site topography," J. Mol. Biol., vol. 262:732-745 (1996).

Mallbris, L. et al., "Molecular insights into fully human and humanized monoclonal antibodies," J. Clin. Aesthet. Dermatol., vol. 9(7):13-15 (2016).

Nair, D. et al., "Epitope Recognition by Diverse Antibodies Suggests Conformational Convergence in an Antibody Response," J. Immunol., vol. 168:2371-2382 (2002).

Yan, J. et al., "Construction of a synthetic phage-displayed naonbody library with CDR3 regions randomized by trimucleotide cassettes for diagnostic applications," J. Transl. Med., vol. 12(343):12 pages (2014).

Altshuler, E.P. et al., "Obtaining recombinant antibodies and methods of increasing their affinity," Advances in Biological Chemistry, vol. 50: 206-207 (2010).

Brown, M. et al., "Tolerance to Single, but Not Multiple, Amino Acid Replacements in Antibody Vh CDR2," The Journal of Immunology, vol. 156:3285-3291 (1996).

Koiko R., Immunology: published by Akademiya, Moscow, pp. 61-62 (2000).

* cited by examiner

5A11 VH chain, SEQ ID NO: 1

AVQLVESGGGLVQPKESLKISCAASGFTFSDAAMYWVRQAPGKGLEWVARIRTKTNNYAAHY
VESVKGRFTVSRDDSKSMVYLQMDNLKTDDTAMYYCTSVPQGTQDYWGQGVMVTVSS

Figure 1a

5A11 VL chain, SEQ ID NO: 2

SYELIQPPSASVTLGNTVSLTCVGDELSKRYVQWSQQKPDKTIVSVIYKDSERPSGISDRFS
GSSSGTTATLTIHGTLAEDEADYYCLSTYSDDNLPVFGGGTKLTVL

Figure 1b

5A11(humanised) VH chain, SEQ ID NO: 13

EVQLVESGGGLVQPGGSLKLSCAASGFTFSDAAMYWVRQASGKGLEWVARIRTKTNNYAAHY
VESVKGRFTVSRDDSKNTVYLQMNSLKTEDTAMYYCTSVPQGTQDYWGQGTLVTVSS

Figure 2a

5A11(humanised) VL chain, SEQ ID NO: 14

SYELTQPSSVSVSPGQTARITCSGDVLSKRYAQWSQQKPGQAIVSVIYKDSERPSGIPERFS
GSSSGTTATLTISGAQVEDEADYYCLSTYADDNLPVFGGGTKLTVL

Figure 2b

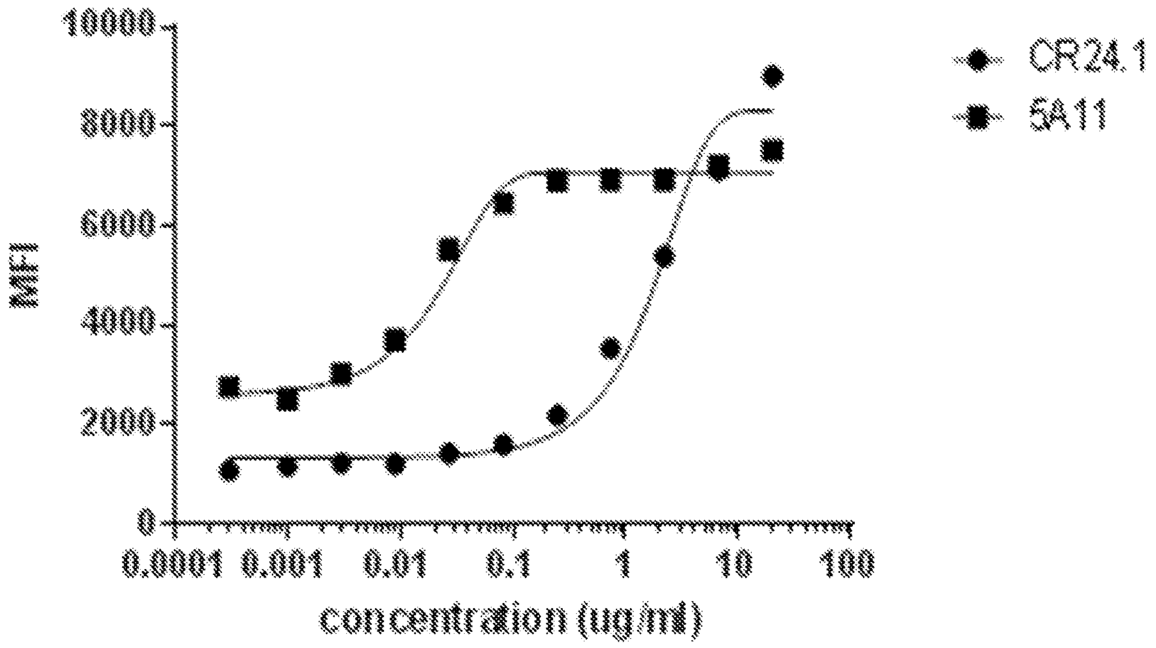

Figure 3

```
SEQ_ID_No1          1 AVQLVESGGGLVQPKESLKISCAASGFTFSDAAMYWVRQAPGKGLEWVAR  50
                      .|||||||||||||..|||:||||||||||||||||||||.|||||||||
SEQ_ID_No13         1 EVQLVESGGGLVQPGGSLKLSCAASGFTFSDAAMYWVRQASGKGLEWVAR  50

SEQ_ID_No1         51 IRTKTNNYAAHYVESVKGRFTVSRDDSKSMVYLQMDNLKTDDTAMYYCTS 100
                      ||||||||||||||||||||||||||||:.|||||::|||:|||||||||
SEQ_ID_No13        51 IRTKTNNYAAHYVESVKGRFTVSRDDSKNTVYLQMNSLKTEDTAMYYCTS 100

SEQ_ID_No1        101 VPQGTQDYWGQGVMVTVSS    119
                      ||||||||||||.:|||||
SEQ_ID_No13       101 VPQGTQDYWGQGTLVTVSS    119
```

Figure 6a

```
SEQ ID NO2          1 SYELIQPPSASVTLGNTVSLTCVGDELSKRYVQWSQQKPDKTIVSVIYKD  50
                      ||||.||.|.||:.|.|..:||.||.|||||.|||||||.:.||||||||
SEQ ID NO14         1 SYELTQPSSVSVSPGQTARITCSGDVLSKRYAQWSQQKPGQAIVSVIYKD  50

SEQ ID NO2         51 SERPSGISDRFSGSSSGTTATLTIHGTLAEDEADYYCLSTYSDDNLPVFG 100
                      |||||||.:|||||||||||||||.|...||||||||||||:||||||||
SEQ ID NO14        51 SERPSGIPERFSGSSSGTTATLTISGAQVEDEADYYCLSTYADDNLPVFG 100

SEQ ID NO2        101 GGTKLTVL    108
                      ||||||||
SEQ ID NO14       101 GGTKLTVL    108
```

Figure 6b

SEQUENCE LISTING

```
Sequence total quantity: 18
SEQ ID NO: 1            moltype = AA  length = 119
FEATURE                 Location/Qualifiers
source                  1..119
                        mol_type = protein
                        organism = Rattus sp.
                        note = Rat
SEQUENCE: 1
AVQLVESGGG LVQPKESLKI SCAASGFTFS DAAMYWVRQA PGKGLEWVAR IRTKTNNYAA  60
HYVESVKGRF TVSRDDSKSM VYLQMDNLKT DDTAMYYCTS VPQGTQDYWG QGVMVTVSS   119

SEQ ID NO: 2            moltype = AA  length = 108
FEATURE                 Location/Qualifiers
source                  1..108
                        mol_type = protein
                        organism = Rattus sp.
                        note = Rat
SEQUENCE: 2
SYELIQPPSA SVTLGNTVSL TCVGDELSKR YVQWSQQKPD KTIVSVIYKD SERPSGISDR  60
FSGSSSGTTA TLTIHGTLAE DEADYYCLST YSDDNLPVFG GGTKLTVL              108

SEQ ID NO: 3            moltype = DNA  length = 411
FEATURE                 Location/Qualifiers
source                  1..411
                        mol_type = unassigned DNA
                        organism = Rattus sp.
                        note = Rat
SEQUENCE: 3
atgttggtgc tgcagtgggt tttggtgact gctctttttc aaggtgttca ttgtgcggta  60
cagcttgttg agtctggtgg aggattggtg cagcctaagg agtcattgaa aatctcatgt  120
gcagcctctg gattcacgtt cagtgatgct gccatgtact gggtccgcca ggctccagga  180
aagggtctgg agtgggttgc gcgcatacga actaaaacta ataattatgc agcgcattat  240
gttgagtcag tgaaaggcag attcaccgtc tccagagatg attcaaaaag catggtctac  300
ctacaaatgg ataacttgaa aactgatgac acagccatgt attactgtac gtcagtcccc  360
caaggaacgc aggattactg gggccaagga gtcatggtca cagtctcctc a           411

SEQ ID NO: 4            moltype = DNA  length = 381
FEATURE                 Location/Qualifiers
source                  1..381
                        mol_type = unassigned DNA
                        organism = Rattus sp.
                        note = Rat
```

```
SEQUENCE: 4
atggcctggg tctctcttgt tctacctctg ctctctctgt atgcaggtta tgtgaccagc  60
tatgagttga tccaaccacc ttcggcatca gtcactctgg gaaatactgt ctcactcact  120
tgtgtcggag atgaattatc aaaaagatat gttcagtggt ctcaacaaaa gccagacaag  180
accattgtgt ccgtgatata caaagatagc gagcggccct caggcatctc tgaccgattc  240
tctggttcca gctccgggac aacagccact ctgacaatcc atggcaccct ggctgaggat  300
gaggctgatt attactgttt gtcaacatat agtgatgata atctccctgt gttcggtggt  360
ggaaccaagc tcactgtcct a                                            381

SEQ ID NO: 5            moltype = AA  length = 5
FEATURE                 Location/Qualifiers
source                  1..5
                        mol_type = protein
                        organism = Rattus sp.
                        note = Rat
SEQUENCE: 5
DAAMY                                                              5

SEQ ID NO: 6            moltype = AA  length = 19
FEATURE                 Location/Qualifiers
source                  1..19
                        mol_type = protein
                        organism = Rattus sp.
                        note = Rat
SEQUENCE: 6
RIRTKTNNYA AHYVESVKG                                               19

SEQ ID NO: 7            moltype = AA  length = 8
FEATURE                 Location/Qualifiers
source                  1..8
                        mol_type = protein
                        organism = Rattus sp.
                        note = Rat
SEQUENCE: 7
VPQGTQDY                                                           8

SEQ ID NO: 8            moltype = AA  length = 11
FEATURE                 Location/Qualifiers
source                  1..11
                        mol_type = protein
                        organism = Rattus sp.
                        note = Rat
SEQUENCE: 8
VGDELSKRYV Q                                                       11

SEQ ID NO: 9            moltype = AA  length = 7
FEATURE                 Location/Qualifiers
source                  1..7
                        mol_type = protein
                        organism = Rattus sp.
                        note = Rat
SEQUENCE: 9
KDSERPS                                                            7

SEQ ID NO: 10           moltype = AA  length = 11
FEATURE                 Location/Qualifiers
source                  1..11
                        mol_type = protein
                        organism = Rattus sp.
                        note = Rat
SEQUENCE: 10
LSTYSDDNLP V                                                       11

SEQ ID NO: 11           moltype = AA  length = 393
FEATURE                 Location/Qualifiers
source                  1..393
                        mol_type = protein
                        organism = Homo sapiens
                        note = Human
SEQUENCE: 11
MWWRVLSLLA WFPLQEASLT NHTETITVEE GQTLTLKCVT SLRKNSSLQW LTPSGFTIFL  60
NEYPALKNSK YQLLHHSANQ LSITVPNVTL QDEGVYKCLH YSDSVSTKEV KVIVLATPFK  120
PILEASVIRK QNGEEHVVLM CSTMRSKPPP QITWLLGNSM EVSGGTLHEF ETDGKKCNTT  180
STLIIHTYGK NSTVDCIIRH RGLQGRKLVA PFRFEDLVTD EETASDALER NSLSSQDPQQ  240
PTSTVSVTED SSTSEIDKEE KEQTTQDPDL TTEANPQYLG LARKKSGILL LTLVSFLIFI  300
LFIIVQLFIM KLRKAHVIWK KENEVSEHTL ESYRSRSNNE ETSSEEKNGQ SSHPMRCMNY  360
ITKLYSEAKT KRKENVQHSK LEEKHIQVPE SIV                                393

SEQ ID NO: 12           moltype = AA  length = 270
```

```
FEATURE                Location/Qualifiers
source                 1..270
                       mol_type = protein
                       organism = Homo sapiens
                       note = Human
SEQUENCE: 12
SLTNHTETIT VEEGQTLTLK CVTSLRKNSS LQWLTPSGFT IFLNEYPALK NSKYQLLHHS  60
ANQLSITVPN VTLQDEGVYK CLHYSDSVST KEVKVIVLAT PFKPILEASV IRKQNGEEHV  120
VLMCSTMRSK PPPQITWLLG NSMEVSGGTL HEFETDGKKC NTTSTLIIHT YGKNSTVDCI  180
IRHRGLQGRK LVAPFRFEDL VTDEETASDA LERNSLSSQD PQQPTSTVSV TEDSSTSEID  240
KEEKEQTTQD PDLTTEANPQ YLGLARKKSG                                  270

SEQ ID NO: 13          moltype = AA  length = 119
FEATURE                Location/Qualifiers
source                 1..119
                       mol_type = protein
                       organism = synthetic construct
                       note = Humanised antibody sequence
SEQUENCE: 13
EVQLVESGGG LVQPGGSLKL SCAASGFTFS DAAMYWVRQA SGKGLEWVAR IRTKTNNYAA  60
HYVESVKGRF TVSRDDSKNT VYLQMNSLKT EDTAMYYCTS VPQGTQDYWG QGTLVTVSS   119

SEQ ID NO: 14          moltype = AA  length = 108
FEATURE                Location/Qualifiers
source                 1..108
                       mol_type = protein
                       organism = synthetic construct
                       note = Humanised antibody sequence
SEQUENCE: 14
SYELTQPSSV SVSPGQTARI TCSGDVLSKR YAQWSQQKPG QAIVSVIYKD SERPSGIPER  60
FSGSSSGTTA TLTISGAQVE DEADYYCLST YADDNLPVFG GGTKLTVL              108

SEQ ID NO: 15          moltype = AA  length = 11
FEATURE                Location/Qualifiers
source                 1..11
                       mol_type = protein
                       organism = synthetic construct
                       note = Humanised CDR sequence
SEQUENCE: 15
SGDVLSKRYA Q                                                      11

SEQ ID NO: 16          moltype = AA  length = 11
FEATURE                Location/Qualifiers
source                 1..11
                       mol_type = protein
                       organism = synthetic construct
                       note = Humanised CDR sequence
SEQUENCE: 16
LSTYADDNLP V                                                      11

SEQ ID NO: 17          moltype = AA  length = 449
FEATURE                Location/Qualifiers
source                 1..449
                       mol_type = protein
                       organism = synthetic construct
                       note = Humanised antibody sequence
SEQUENCE: 17
EVQLVESGGG LVQPGGSLKL SCAASGFTFS DAAMYWVRQA SGKGLEWVAR IRTKTNNYAA  60
HYVESVKGRF TVSRDDSKNT VYLQMNSLKT EDTAMYYCTS VPQGTQDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVEH EDPEVKFNWY VDGVEVHNAK TKPREEQYNS  300
TYRVVSVLTV LHQDWLNGKE YKCKVSNKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 18          moltype = AA  length = 214
FEATURE                Location/Qualifiers
source                 1..214
                       mol_type = protein
                       organism = synthetic construct
                       note = Humanised antibody sequence
SEQUENCE: 18
SYELTQPSSV SVSPGQTARI TCSGDVLSKR YAQWSQQKPG QAIVSVIYKD SERPSGIPER  60
FSGSSSGTTA TLTISGAQVE DEADYYCLST YADDNLPVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                             214
```

CRTAM ANTIBODIES AND METHODS OF TREATING CANCER

RELATED APPLICATIONS PARAGRAPH

This application is a Continuation of U.S. patent application Ser. No. 16/760,180, filed Apr. 29, 2020, pending, which application claims priority to 35 U.S.C. 371 national stage filing of International Application No. PCT/GB2018/053165, filed on Nov. 1, 2018, which claims the benefit of the priority date of U.S. Provisional Application No. 62/580,667, filed on Nov. 2, 2017, and U.S. Provisional Application No. 62/697,145, filed on Jul. 12, 2018, the contents of each of which are hereby incorporated by reference in their entirety.

SEQUENCE LISTING

The instant application contains a Sequence Listing which has been submitted electronically in XML format and is hereby incorporated by reference in its entirety. Said XML copy, created on May 17, 2023, is named OTJ-019US-CN_SL.xml and is 22,108 bytes in size.

FIELD OF THE INVENTION

The present invention relates to antibodies that are capable of binding to a CRTAM protein, and their uses.

INTRODUCTION

Aspects of the invention include antibodies and other therapeutic proteins directed against CRTAM, nucleic acids encoding such antibodies and therapeutic proteins, methods for preparing antibodies and other therapeutic proteins, and methods for the treatment of diseases, such as cancers, by using antibodies and other therapeutic proteins directed against CRTAM.

BACKGROUND OF THE INVENTION

The target antigen, CRTAM, is a single-pass type I membrane protein of the nectin family with V and C1-like Ig domains (Yeh et al., Cell. 2008 Mar. 7; 132(5):846-5). The gene was first identified in mouse and human activated NKT cells (Kennedy et al, J Leukoc Biol. 2000 May; 67(5):725-34) with subsequent studies showing its expression to be tightly regulated by activation and restricted to activated class-I MHC-restricted cells including NKT and CD8 T cells (Patiño-Lopez et al, J Neuroimmunol. 2006 February; 171(1-2):145-55).

The only known ligand of CRTAM is Necl2 (Galibert et al, J Biol Chem. 2005 Jun. 10; 280(23):21955-64), and the interaction between the ligand and receptor is thought to be preferred over homophylic interactions of either molecule (Zhang et al, Structure. 2013 Aug. 6; 21(8):1430-9). The CRTAM-Necl2 interaction is hypothesised to help establishment of a mature immune synapse and aid enhancement of T-cell stimulation by non-professional APCs. This function has also been seen in NK cells where antibodies directed towards CRTAM have stimulated NK cell cytotoxicity (Boles et al, Blood. 2005 Aug. 1; 106(3):779-86). WO2009/029883 discloses that CRTAM is upregulated on a specific set of T cells and selectively regulates certain cytokines including IFNγ, IL22 and IL17. WO2016/154341 discloses that agonistic anti CRTAM antibodies may be useful for the treatment of cancer by augmenting the ADCC capability of immune effector cells such as NK cells.

SUMMARY

Aspects of the invention include specific antibodies directed against CRTAM, nucleic acids encoding such antibodies of the invention, host cells comprising such nucleic acids encoding an antibody of the invention, methods for preparing anti-CRTAM antibodies, and methods for the treatment of diseases, e.g., human cancers, including but not limited to small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers and stomach cancer, glioma, glioblastoma, testicular, thyroid, bone, gallbladder and bile ducts, uterine, adrenal cancers, sarcomas, GIST, neuroendocrine tumours, and haematological malignancies.

Described herein there is provided an antibody that binds to CRTAM (SEQ ID NO:11). Preferably, said antibody binds to the extracellular domain of CRTAM (SEQ ID NO: 12). Aspects of the invention include an antibody, or an antigen binding fragment thereof, which binds to an epitope on the CRTAM protein recognized by an antibody described herein, or which cross-competes for binding with an antibody described herein, and which preferably retains at least about 80%, at least about 85%, at least about 90%, at least about 91%, at least about 92%, at least about 93%, at least about 94%, at least about 95%, at least about 96%, at least about 97%, at least about 98% or at least about 99%, of the binding affinity for human CRTAM of an antibody described herein. In some embodiments the antibody is an isolated antibody.

Aspects of the invention include an antibody, or an antigen-binding fragment thereof, that binds to CRTAM, said antibody comprising a heavy chain variable region comprising: a CDR-H1 sequence comprising the sequence of SEQ ID NO: 5; a CDR-H2 sequence comprising SEQ ID NO: 6; and a CDR-H3 sequence comprising the sequence of SEQ ID NO: 7. In some embodiments, the antibody or antigen-binding fragment further comprises a light chain variable region comprising at least one CDR sequence selected from the group consisting of: CDR-L1 comprising any one of the sequences of SEQ ID NO: 8, or SEQ ID NO: 15; CDR-L2 comprising the sequence of SEQ ID NO: 9; and CDR-L3 comprising any one of the sequences of SEQ ID NO: 10, or SEQ ID NO: 16.

In some embodiments, the antibody, or antigen-binding fragment thereof, that binds to CRTAM comprises a heavy chain variable region and a light chain variable region comprising one of the 4 combinations of heavy and light chain CDRs as shown in Table 1

TABLE 1

| | Heavy Chain Variable Region CDRs | | | Light Chain Variable Region CDRs | | |
|---|---|---|---|---|---|---|
| | CDR-H1 | CDR-H2 | CDR-H3 | CDR-L1 | CDR-L2 | CDR-L3 |
| 1 | SEQ ID NO: 5 | SEQ ID NO: 6 | SEQ ID NO: 7 | SEQ ID NO: 8 | SEQ ID NO: 9 | SEQ ID NO: 10 |

TABLE 1-continued

| | Heavy Chain Variable Region CDRs | | | Light Chain Variable Region CDRs | | |
|---|---|---|---|---|---|---|
| | CDR-H1 | CDR-H2 | CDR-H3 | CDR-L1 | CDR-L2 | CDR-L3 |
| 2 | SEQ ID NO: 5 | SEQ ID NO: 6 | SEQ ID NO: 7 | SEQ ID NO: 15 | SEQ ID NO: 9 | SEQ ID NO: 16 |
| 4 | SEQ ID NO: 5 | SEQ ID NO: 6 | SEQ ID NO: 7 | SEQ ID NO: 8 | SEQ ID NO: 9 | SEQ ID NO: 16 |
| 5 | SEQ ID NO: 5 | SEQ ID NO: 6 | SEQ ID NO: 7 | SEQ ID NO: 15 | SEQ ID NO: 9 | SEQ ID NO: 10 |

In some preferred embodiments, the antibody, or antigen-binding fragment thereof, that binds to CRTAM comprises a heavy chain variable region comprising a CDR-H1 comprising SEQ ID NO:5; a CDR-H2 comprising SEQ ID NO:6; and a CDR-H3 comprising SEQ ID NO:7; and a light chain variable region comprising a CDR-L1 comprising SEQ ID NO:8; a CDR-L2 comprising SEQ ID NO:9; and a CDR-L3 comprising SEQ ID NO:10.

In another preferred embodiment, the antibody, or antigen-binding fragment thereof, that binds to CRTAM comprises a heavy chain variable region comprising a CDR-H1 comprising SEQ ID NO:5; a CDR-H2 comprising SEQ ID NO:6; and a CDR-H3 comprising SEQ ID NO:7; and a light chain variable region comprising a CDR-L1 comprising SEQ ID NO:15; a CDR-L2 comprising SEQ ID NO:9; and a CDR-L3 comprising SEQ ID NO:16.

In a further aspect, the antibodies, or antigen-binding fragments thereof, of the invention comprise variable CDRs as compared to the parent antibody described herein. Thus, the invention provides variant antibodies, or antigen-binding fragments thereof, comprising variant variable regions of a parent antibody, wherein the parent antibody, or antigen-binding fragment thereof, comprises a heavy chain variable region comprising: a CDR-H1 sequence comprising the sequence of SEQ ID NO: 5; a CDR-H2 sequence comprising the sequence of SEQ ID NO: 6; and a CDR-H3 sequence comprising the sequence of SEQ ID NO: 7; and a light chain variable region comprising a CDR-L1 comprising the sequence of SEQ ID NO: 15; CDR-L2 comprising the sequence of SEQ ID NO: 9; and CDR-L3 comprising the sequence of SEQ ID NO: 16, and wherein in one embodiment the variant antibody, or antigen-binding fragment thereof, has 1, 2, 3, 4, 5 or 6 amino acid substitutions, additions and or deletions in any one or more of; or 1, 2, 3, 4, 5, 6, 7, 8, 9, 10, 11, 12 amino acid substitutions, additions and or deletions collectively in; the set of CDR-H1, CDR-H2, CDR-H3, CDR-L1, CDR-L2 and CDR-L3, with from 1 to 5 or 1 to 4 or 1 to 3 substitutions additions or deletions of particular use, and wherein the antibody, or antigen-binding fragment thereof, retains specific binding to CRTAM. Preferably the variations are substitutions, preferably, the substitutions are conservative substitutions or substitutions to revert an amino acid in the variable region back to the corresponding amino acid from the human germline. In a further embodiment, the variant antibody, or antigen-binding fragment thereof, of the invention comprises: a CDR-H1 sequence comprising the sequence of SEQ ID NO: 5; a CDR-H2 sequence comprising the sequence of SEQ ID NO: 6; and a CDR-H3 sequence comprising the sequence of SEQ ID NO: 7; and a light chain variable region comprising a CDR-L1 comprising the sequence of SEQ ID NO: 15; CDR-L2 comprising the sequence of SEQ ID NO: 9; and CDR-L3 comprising the sequence of SEQ ID NO: 16, wherein one or more of said CDR sequences is altered such that it is about 70, 75, 80, 85, 87, 88, 89, 90, 91, 92, 93, 94, 95, 96, 97, 98, 99% identical to the corresponding CDR parental sequence recited above.

In some embodiments there is provided an antibody, or antigen-binding fragment thereof, comprising a variable heavy chain region described in SEQ ID NO: 1 or SEQ ID NO: 13, or a sequence that is about 80, 85, 90, 91, 92, 93, 94, 95, 96, 97, 98, 99% identical to SEQ ID NO: 1 or SEQ ID NO: 13 and/or a variable light chain region described in SEQ ID NO: 2, or SEQ ID NO: 14, or a sequence that is about 80, 85, 90, 91, 92, 93, 94, 95, 96, 97, 98, 99% identical to SEQ ID NO: 2, or SEQ ID NO: 14. In further embodiments there is provided an antibody, or antigen-binding fragment thereof, comprising a heavy chain variable region that comprises 1, 2, 3, 4, 5, 6, 7, 8, 9, 10, 11 or 12 amino acid substitutions, additions and/or deletions compared to SEQ ID NO: 1 or SEQ ID NO: 13 and/or a variable light chain region that comprises 1, 2, 3, 4, 5, 6, 7, 8, 9, 10, 11 or 12 amino acid substitutions compared to SEQ ID NO: 2, or SEQ ID NO: 14. Preferably, substitutions, more preferably conservative substitutions.

It will further be apparent that the amino acid substitutions, additions and/or deletions can be within the framework regions and/or within the CDRs.

In one embodiment there is provided an antibody, or antigen-binding fragment thereof comprising a heavy chain variable region comprising the sequence of SEQ ID NO: 1, and a light chain variable region comprising the sequence of SEQ ID NO: 2.

In one embodiment there is provided an antibody, or antigen-binding fragment thereof comprising a heavy chain variable region comprising the sequence of SEQ ID NO: 13, and a light chain variable region comprising the sequence of SEQ ID NO: 14.

In one embodiment there is provided a full length antibody comprising a heavy chain sequence comprising SEQ ID NO:17 and a light chain sequence comprising SEQ ID NO: 18.

In a further aspect of the present invention there is provided an antibody, or antigen binding-fragment thereof that specifically binds to CRTAM, said antibody comprising the 3 heavy chain CDRs of SEQ ID NO:1 or SEQ ID NO:13 and the 3 light chain CDRs of SEQ ID NO:2, or SEQ ID NO:14 wherein the CDRs are defined by the Kabat or by the Chothia numbering system. Preferably, said antibody, or antigen binding-fragment thereof that specifically binds to CRTAM, comprises the 3 heavy chain CDRs of SEQ ID NO:13 and the 3 light chain CDRs or SEQ ID NO:14 defined by the Kabat or by the Chothia numbering system.

SEQ ID NOs:13-18 are humanised antibody sequences based on the sequences of SEQ ID Nos: 1 and 2. The skilled person would readily understand that SEQ ID Nos: 17-18 are full length heavy and light chain sequences including the regions other than the variable regions which are required to produce a full length functional antibody i.e the constant and Fc regions. The skilled person will understand that the sequences are humanised by replacing amino acids from the variable region of the organism in which the antibody is produced with amino acids from the human germ line sequence in an effort to minimise the immunogenic effects of the antibodies when these are administered to human subjects. The majority of amino acid substitutions occur in the framework region however a number of amino acids from the CDRs, which occur in non-critical positions, can be substituted; such substitutions are preferably conservative in nature or revert an amino acid at a particular position to the amino acid present in the corresponding human germline. In the present case the amino acids from the CDRs which have been substituted have been identified using structural models to discriminate between paratope facing and non-paratopic residues in the CDR region. This allows the antibodies to be humanised to a higher degree than by simple CDR grafting.

In the present invention SEQ ID NO:14 comprises 3 amino acid substitutions in CDR 1 (SEQ ID NO:15) when compared to CDR1 of SEQ ID NO:2 (SEQ ID NO:8). Specifically there is a V-S substitution at position 1 of SEQ ID NO:8; an E-V substitution at position 4 of SEQ ID NO:8; and a V-A substitution at position 10 of SEQ ID NO:8. SEQ ID NO:14 further comprises 1 amino acid substitution in CDR3 (SEQ ID NO:16) when compared to CDR3 of SEQ ID NO:2 (SEQ ID NO:10). Specifically there is a S-A substitution at position 5 of SEQ ID NO:10.

It will be understood by the skilled person that these humanised sequences do not represent different, alternative, antibodies when compared to the parental antibody, but relate to the same antibody having the same characteristics which has merely been altered to correspond more closely to the human germline using structural modelling in order to minimise immunogenicity.

In some embodiments, the antibody, or antigen-binding fragment has a binding affinity ($K_D$) of 5 nM, 4 nM, 3 nM, 2 nM, 1 nM or less, in a preferred embodiment the binding affinity is 0.75 nM, 0.5 nM or less.

In some embodiments, the antibody, or antigen-binding fragment of the invention is an antibody or antigen binding fragment which competes for binding to CRTAM with its ligand necl2.

In some embodiments, an antibody, or antigen-binding fragment, is a monoclonal antibody. In some embodiments, an antibody is a chimeric, humanized, or human antibody.

In some embodiments, a heavy chain variable region comprises a framework sequence. In some embodiments, at least a portion of the framework sequence comprises a human consensus framework sequence. In some embodiments, a light chain variable region comprises a framework sequence. In some embodiments, at least a portion of the framework sequence comprises a human consensus framework sequence.

In some embodiments, the antibody or antigen binding fragment is an Fc variant engineered to have increased binding to FcgRIIa. In one preferred embodiment the Fc variant comprises S267E and/or L328F amino acid substitutions. In one embodiment the Fc is an IgG1 Fc region. In a further embodiment the Fc is an IgG4 Fc region. In a preferred embodiment, when the Fc region is an IgG4 Fc region, the Fc region will further comprise a S228P substitution. In one embodiment the heavy chain comprises a sequence comprising SEQ ID NO: 17.

In some embodiments, the antibody, or antigen-binding fragment, is an Fc silenced engineered IgG1 antibody or antigen-binding fragment having reduced or no binding to one or more Fc receptors. In another embodiment the antibody is an IgG4 antibody.

In some embodiments, the antibody, or antigen-binding fragment, is a bispecific antibody or antigen-binding fragment that mediates T-cell cytotoxicity and/or NK cell cytotoxicity.

In some embodiments, the antibody, or antigen-binding fragment, is capable of inducing and/or enhancing activation of an immune cell. In one embodiment the immune cell is preferably a T cell. In another embodiment the immune cell is preferably an NK cell. The skilled person will understand that the term inducing and/or enhancing can refer to inducing and/or enhancing cytokine release by an immune cell and/or inducing and/or enhancing proliferation of said immune cell and/or inducing and/or enhancing cell killing activity. It will be readily apparent to the skilled person that the term induce or inducing as used in the present context means causing activation of an immune cell or increasing activation of an immune cell to above the level of activation seen in the absence of the antibody or antigen-binding fragment. The term enhancing as used in the present context refers to increasing the level of activation of an already activated immune cell.

In some embodiments, the antibody, or antigen-binding fragment, is a bispecific or multispecific antibody or antigen-binding fragment that binds to a CRTAM protein and binds to one or more additional binding targets preferably said additional binding targets are one or more tumor antigens. In a further embodiment the one or more additional binding targets are immunomodulatory molecules.

In some embodiments, an antigen-binding fragment is selected from the group consisting of: Fab, Fab', $F(ab)_2$, $F(ab')_2$, Fv, scFv, dAb and single-domain antibody.

In another aspect of the present invention there is provided one or more nucleic acids encoding a heavy chain of an antibody of the invention and/or a light chain of an antibody of the invention. It will be understood that the heavy and light chains of the antibody of the invention can be encoded together on a single nucleic acid molecule or by two separate nucleic acid molecules.

In another aspect vectors comprising one or more of the nucleic acids of the invention are provided.

In another aspect of the present invention there is provided a host cell containing the one or more nucleic acid(s) encoding the heavy and/or light chain, or both, of the antibodies of the invention. In some embodiments said host cell is grown under conditions wherein the nucleic acid(s) is expressed. In other embodiments, a method of recovering the antibody of the invention is provided.

Aspects of the invention include methods of making an antibody, or an antigen-binding fragment thereof, the methods comprising culturing a host cell under conditions wherein the antibody, or the antigen-binding fragment, is expressed in the host cell, and optionally isolating the antibody or antigen-binding fragment.

Aspects of the invention include pharmaceutical compositions comprising an antibody, or antigen-binding fragment, as described herein and a pharmaceutically-acceptable carrier.

In some embodiments, a pharmaceutical composition or medicament further comprises an effective amount of a second therapeutic agent.

In a further aspect of the present invention there is provided a method of treating a disorder, said method comprising administering to a patient in need thereof an antibody or antigen-binding fragment of the invention which binds to CRTAM (SEQ ID NO:11). In one embodiment the disorder is cancer.

In a further aspect there is provided a method of treating cancer comprising administering an effective amount of an antibody or antigen-binding fragment of the invention to a subject in need thereof.

In one embodiment, the antibody or antigen-binding fragment comprises a heavy chain variable region comprising a CDR-H1 comprising SEQ ID NO:5; a CDR-H2 comprising SEQ ID NO:6, and a CDR-H3 comprising SEQ ID NO:7 and a light chain variable region comprising a CDR-1 comprising SEQ ID NO:8, or SEQ ID NO:15, a CDR-L2 comprising SEQ ID NO:9 and a CDR-L3 comprising SEQ ID NO:10, or SEQ ID NO:16. Preferably, the light chain variable region comprises a CDR-1 comprising SEQ ID NO:15, a CDR-L2 comprising SEQ ID NO:9 and a CDR-L3 comprising SEQ ID NO:16

In some embodiments a method of treating cancer is provided, wherein a patient in need thereof is administered an antibody or antigen-binding fragment of the invention and wherein said antibody or antigen-binding fragment of the invention induces and/or enhances an immune response, for example, a cytotoxic T-cell response and/or an NK cell response.

In some embodiments, the cancer is selected from the group consisting of small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

According to a further aspect of the invention there is provided an antibody or antigen-binding fragment of the present invention for use in prophylaxis or therapy.

Preferably, the antibody or antigen-binding fragment is for use in the prophylaxis or therapy of cancer.

According to a further aspect of the present invention there is provided the use of an antibody or antigen-binding fragment according to the present invention in the manufacture of a medicament for the treatment of cancer.

In some embodiments, the cancer according to the previous aspects is selected from the group consisting of small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

BRIEF DESCRIPTION OF THE DRAWINGS

FIG. 1*a* shows the amino acid sequence of the variable region of the heavy chain of the parental 5A11 antibody (SEQ ID NO:1).

FIG. 1*b* shows the amino acid sequence of the variable region of the light chain of the parental 5A11 antibody (SEQ ID NO:2).

FIG. 2*a* shows the amino acid sequence of the variable region of the heavy chain of the humanised antibody 5A11 (SEQ ID NO:13).

FIG. 2*b* shows the amino acid sequence of the variable region of the light chain of the humanised antibody 5A11 (SEQ ID NO:14).

FIG. 3 shows specific dose-related binding of antibody 5A11 and the commercially available anti-CRTAM antibody CR24.1 to activated T cells.

FIG. 6*a* shows a sequence alignment of the heavy chain variable region of the 5A11 parental antibody sequence and the humanised heavy chain variable region 5A11 sequence.

FIG. 6*b* shows a sequence alignment of the light chain variable region of the 5A11 parental antibody sequence and the humanised light chain variable region 5A11 sequence.

DETAILED DESCRIPTION

Figure 4:
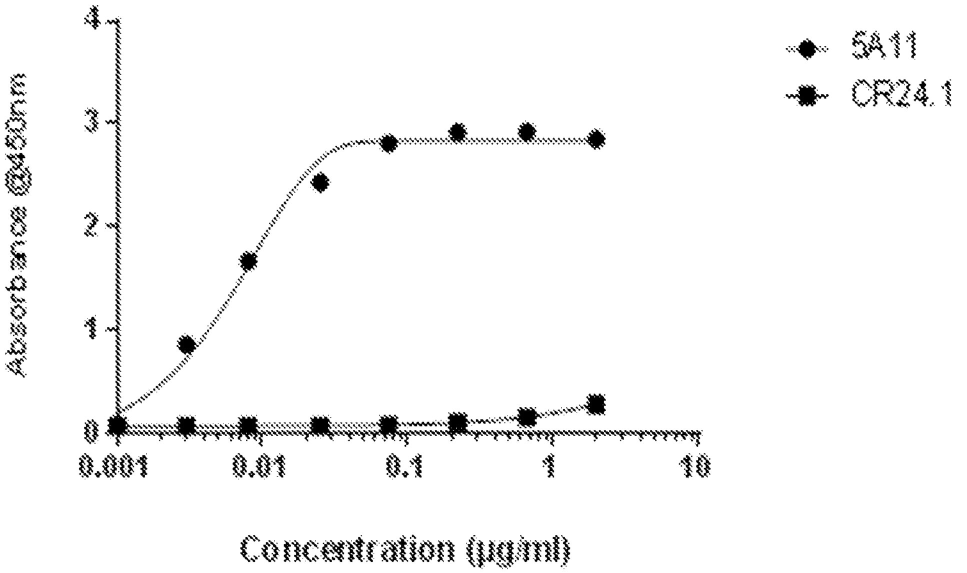
FIG. 4 shows that antibody 5A11 cross reacts with cynomolgous monkey CRTAM homologue whereas antibody CR24.1 does not.

Aspects of the invention include antibodies directed against CRTAM, nucleic acids encoding such antibodies, host cells comprising such nucleic acids encoding an antibody of the invention, methods for preparing anti-CRTAM antibodies, and methods for the treatment of diseases, such as CRTAM-mediated disorders, e.g., human cancers, including but not limited to small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

It is noted that, as used herein and in the appended claims, the singular forms "a", "an", and "the" include plural references unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

Definitions

For purposes of interpreting this specification, the following definitions will apply and whenever appropriate, terms used in the singular will also include the plural and vice versa.

The term "CRTAM", as used herein, refers to any native CRTAM protein from any vertebrate source, including mammals such as primates (e.g., humans, primates, and rodents (e.g., mice and rats)), unless otherwise indicated. The CRTAM protein can also be referred to as a CRTAM-like protein. The amino acid sequence of human CRTAM is provided herein in SEQ ID NO: 11.

The term "CRTAM" encompasses "full-length" unprocessed CRTAM as well as any form of CRTAM that results from processing in the cell. The term also encompasses naturally occurring variants of CRTAM, e.g., splice variants, allelic variants and isoforms. The term specifically includes naturally-occurring truncated or secreted forms of the CRTAM polypeptide (e.g., an extracellular domain sequence). The CRTAM polypeptides described herein may be isolated from a variety of sources, such as from human tissue types or from another source, or prepared by recombinant or synthetic methods. A "native sequence CRTAM polypeptide" comprises a polypeptide having the same amino acid sequence as the corresponding CRTAM polypeptide derived from nature. Such native sequence CRTAM polypeptides can be isolated from nature or can be produced by recombinant or synthetic means. The term "CRTAM epitope" as used herein refers to an epitope bound by an antibody comprising at least one or more of the CDR sequences described herein, and/or as exemplified by the binding profile of an anti-CRTAM antibody as illustrated in the examples.

The term "antibody" is used in the broadest sense and specifically covers, for example, single anti-CRTAM monoclonal antibodies (including agonist, antagonist, neutralizing antibodies, full length or intact monoclonal antibodies), anti-CRTAM antibody compositions with polyepitopic specificity, polyclonal antibodies, multivalent antibodies, multispecific antibodies (e.g., bispecific antibodies so long as they exhibit the desired biological activity), formed from at least two intact antibodies, single chain anti-CRTAM antibodies, and antigen binding fragments of anti-CRTAM antibodies, including Fab, Fab', F(ab')2 and Fv fragments, diabodies, single domain antibodies (sdAbs), as long as they exhibit the desired biological or immunological activity. The term "immunoglobulin" (Ig) is used interchangeably with the term "antibody" herein. An antibody can be chimeric, human, humanized and/or affinity matured. It will be appreciated by those of ordinary skill in the art that in some embodiments at a minimum antibodies contain a set of 6 CDRs as defined herein; they include, but are not limited to, traditional antibodies (including both monoclonal and polyclonal antibodies), humanized, human and/or chimeric antibodies, antibody fragments, engineered antibodies (e.g., with amino acid modifications as outlined below), multispecific antibodies (including bispecific antibodies), and other analogues known in the art and discussed herein.

It will be understood that in other embodiments the term antibody as used herein refers to structures which do not comprise 6 CDRs; including, but not limited to, Nanobody®, Unibody® and scFv fragments.

The term "anti-CRTAM antibody", "CRTAM antibody", or "an antibody that binds to CRTAM" refers to an antibody that is capable of binding CRTAM with sufficient affinity such that the antibody is useful as a diagnostic and/or therapeutic agent in targeting CRTAM. In certain embodiments, an anti-CRTAM antibody binds to an epitope of CRTAM that is conserved among CRTAM from different species.

An "isolated antibody" is one which has been identified and separated and/or recovered from a component of its environment. Contaminant components of its environment are materials which would interfere with therapeutic uses for the antibody, and may include enzymes, hormones, and other proteinaceous or non-proteinaceous solutes.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity.

The term "antagonist" is used in the broadest sense, and includes any molecule that partially or fully blocks, inhibits, or neutralizes a biological activity of a native CRTAM polypeptide. Suitable antagonist molecules specifically include antagonist antibodies or antibody fragments, fragments or amino acid sequence variants of native CRTAM polypeptides, peptides, antisense oligonucleotides, small organic molecules, etc. Methods for identifying antagonists of a CRTAM polypeptide, may comprise contacting an CRTAM polypeptide with a candidate antagonist molecule and measuring a detectable change in one or more biological activities normally associated with the CRTAM polypeptide.

The term "agonist" is used in the broadest sense, and includes any molecule that enhances a biological activity of a native CRTAM polypeptide. Suitable agonist molecules specifically include agonist antibodies or antibody fragments, fragments or amino acid sequence variants of CRTAM ligand polypeptides, peptides, antisense oligonucleotides, small organic molecules, etc. Methods for identifying agonists of a CRTAM polypeptide, may comprise contacting a CRTAM polypeptide with a candidate agonist molecule and measuring a detectable change in one or more biological activities normally associated with the CRTAM polypeptide.

"Tumor", as used herein, refers to all neoplastic cell growth and proliferation, whether malignant or benign, and all pre-cancerous and cancerous cells and tissues. The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-cancer agent, including an anti-CRTAM antibody.

CRTAM Proteins

According to SWISS-PROT, CRTAM is a type I membrane protein of the nectin family. The protein consists of one Ig-like V-type (immunoglobulin-like) domain, one Ig-like C-type (immunoglobulin-like) domain (Yeh et al., Cell. 2008 Mar. 7; 132(5):846-5), one transmembrane region and an extracellular tail between amino acids 18-287 of SEQ ID No: 11.

The gene was first identified in mouse and human activated NKT cells (Kennedy et al, J Leukoc Biol. 2000 May;

67(5):725-34) with subsequent studies showing its expression tightly regulated by activation and restricted to activated class-I MHC-restricted cells including NKT and CD8 T cells (Patiño-Lopez et al, J Neuroimmunol. 2006 February; 171(1-2):145-55). The only known ligand of CRTAM is Necl2 (Galibert et al, J Biol Chem. 2005 Jun. 10; 280(23): 21955-64), and the interaction between the ligand and the receptor is thought to be preferred over homophylic interactions of either molecule (Zhang et al, Structure. 2013 Aug. 6; 21(8):1430-9). The CRTAM-Necl2 interaction is hypothesised to help establishment of a mature immune synapse and aid enhancement of T-cell stimulation by non-professional APCs. This function has also been seen in NK cells where antibodies directed towards CRTAM have stimulated NK cell cytotoxicity (Boles et al, Blood. 2005 Aug. 1; 106(3):779-86).

In some embodiments, an antibody of the invention binds to human CRTAM. "Human CRTAM" or "Human CRTAM protein" as used herein refers to the protein of SEQ ID NO:11, as defined herein.

An antibody in accordance with embodiments of the invention may, in certain cases, cross-react with a CRTAM protein from a species other than a human. For example, to facilitate pre-clinical and toxicology testing, an antibody of the invention may cross react with murine or primate CRTAM proteins. Alternatively, in certain embodiments, an antibody may be specific for a human CRTAM protein and may not exhibit species or other types of non-human cross-reactivity.

Antibodies

Aspects of the invention include anti-CRTAM antibodies, generally therapeutic and/or diagnostic antibodies, as described herein. Antibodies that find use in the methods of the present invention can take on any of a number of formats as described herein, including traditional antibodies as well as antibody derivatives, antigen-binding fragments and mimetics, as further described herein. In some embodiments, an antibody has one or more CDRs selected from a set of 6 CDRs as defined herein (including small numbers of amino acid changes as described herein). As reviewed above, the term "antibody" as used herein refers to a variety of structures.

In some embodiments, IgG isotypes are used in the present invention. In one embodiment Fc silenced IgG1 isotype antibodies are used. In another embodiment IgG4 isotype antibodies are used.

The amino-terminal portion of each chain of an antibody includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (CDR-L1; "L" denotes light chain), 50-56 (CDR-L2) and 89-97 (CDR-L3) in the light chain variable region and around about 31-35B (CDR-H1; "H" denotes heavy chain), 50-65 (CDR-H2), and 95-102 (CDR-H3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g., residues 26-32 (CDR-L1), 50-52 (CDR-L2) and 91-96 (CDR-L3) in the light chain variable region and 26-32 (CDR-H1), 53-55 (CDR-H2) and 96-101 (CDR-H3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g., Kabat et al., supra (1991)).

The CDRs contribute to the formation of the antigen-binding, or more specifically, epitope binding site of antibodies. A single antigen may have more than one epitope.

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, amino acid modifications are made to the Fc region, for example to alter binding to one or more FcγR receptors or to the FcRn receptor. In some embodiments, the antibodies are full length. By "full length antibody" herein is meant the structure that constitutes the natural biological form of an antibody, including variable and constant regions, optionally including one or more modifications as outlined herein.

Alternatively, the antibodies can be a variety of structures, including, but not limited to, antigen-binding fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and antigen binding fragments of each, respectively. Structures that rely on the use of a set of CDRs are included within the definition of "antibody".

In one embodiment, an antibody is an antigen-binding fragment. Specific antigen-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable region, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all incorporated by reference in their entirety).

Chimeric and Humanized Antibodies

In some embodiments, an antibody can be a mixture from different species, e.g., a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536, all entirely incorporated by reference. "In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising an scFv joined to a CH3 domain. Hu et al., 1996, Cancer Res. 56:3055-3061, entirely incorporated by reference. In some cases, the scFv can be joined to the Fc region, and may include some or the entire hinge region. It should be noted that minibodies are included within the definition of "antibody" despite the fact it does not have a full set of CDRs.

The antibodies of the present invention are generally isolated or recombinant.

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to CRTAM is substantially free of antibodies that specifically bind antigens other than CRTAM.

Isolated monoclonal antibodies, having different specificities, can be combined in a well-defined composition. Thus for example, an antibody of the invention can optionally and individually be included or excluded in a formulation, as is further discussed below.

Specific binding for a particular antigen or an epitope can be exhibited, for example, by an antibody having a $K_D$ for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000- or more times lower for the antigen or epitope relative to a control molecule.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000- or more times greater for the epitope relative to a control, where $K_A$ or $K_a$ refers to an association rate of a particular antibody-antigen interaction.

Standard assays to evaluate the binding ability of the antibodies toward CRTAM can be done on the protein or cellular level and are known in the art, including for example, ELISAs, Western blots, RIAs, Octet®, BIAcore® assays and flow cytometry analysis. Suitable assays are described in detail in the Examples. The binding kinetics (e.g., binding affinity) of the antibodies also can be assessed by standard assays known in the art, such as by Biacore® or Octet® system analysis.

CRTAM Antibodies

The present invention provides CRTAM antibodies that bind to a CRTAM polypeptide or portion thereof. An example of a CRTAM amino acid sequence is provided in SEQ ID NO: 11. The subject CRTAM antibodies can induce or enhance immune cell activation, for example, T cell activation and/or NK cell activation, to enhance the immune response in the tumor. These antibodies are referred to herein either as "anti-CRTAM" antibodies or, for ease of description, "CRTAM antibodies".

In some embodiments, a subject CRTAM antibody can induce and/or enhance cytokine release or proliferation upon contact with T cells, particularly CD8+ T cells which express CRTAM on their surface. Cytokine release or T cell proliferation in this context can be measured in several ways. In one embodiment, a CRTAM antibody of the invention is contacted with activated T cells, using standard assays such as ELISA. In a further embodiment a subject CRTAM antibody can induce and/or enhance NK cell activation and killing.

In one embodiment, the antibody is an antibody comprising the following CDRs; in addition, as discussed below, these CDR sequences can also contain a limited number of amino acid variants as previously described:

| CDR | SEQ ID NO: |
|---|---|
| 5A11_VH_CDR1 | SEQ ID NO: 5 |
| 5A11_VH_CDR2 | SEQ ID NO: 6 |
| 5A11_VH_CDR3 | SEQ ID NO: 7 |
| 5A11_VL_CDR1 | SEQ ID NO: 15 |
| 5A11_VL_CDR2 | SEQ ID NO: 9 |
| 5A11_VL_CDR3 | SEQ ID NO: 16 |

In some embodiments, an antibody comprises an amino acid sequence of at least one or more of the CDR sequences provided in SEQ ID NOS: 5, 6, 7, 15, 9 and 16. In some embodiments, an antibody comprises an amino acid sequence that is at least about 75%, 80%, 85%, 90%, 95%, 96%, 97%, 98% or 99% identical to an amino acid sequence of one or more of the CDR sequences provided in SEQ ID NOS: 5, 6, 7, 15, 9 and 16.

Disclosed herein are also variable heavy and light chains that comprise the CDR sets of the invention, as well as full length heavy and light chains (e.g., comprising constant regions as well). As will be appreciated by those in the art, the CDR sets of the invention can be incorporated into murine, humanized or human constant regions (including framework regions). Aspects of the invention include heavy chain variable regions and light chain variable regions that are at least about 80%, 85%, 90%, 95%, 96%, 97%, 98% or 99% identical to the heavy chain variable region sequence (SEQ ID NO: 13) and light chain variable region sequence (SEQ ID NO: 14) disclosed herein.

In some embodiments, the invention provides antibodies that bind to the same epitope on human CRTAM as, or that cross compete with, the CRTAM monoclonal antibody of the invention described herein (i.e., antibodies that have the ability to cross-compete for binding to an CRTAM protein with the monoclonal antibody of the invention described herein). In some embodiments, the reference antibody for cross-competition studies can be the 5A11 antibody as defined herein. Such cross-competing antibodies can be identified based on their ability to cross-compete with the 5A11 antibody. It will be understood that for an antibody to be considered to cross compete, it does not necessarily completely block binding of the reference antibody. In some embodiments, binding of a reference antibody is reduced by at least about 10, 20, 30, 40, 50, 60, 70, 75, 80, 85, 90, 95, 97, 98 or 99%. In some embodiments, the invention provides an antibody or antigen binding fragment thereof that competes for binding to CRTAM with the ligand necl2.

Antibody Modifications

The present invention further provides variant antibodies, sometimes referred to as "antibody derivatives" or "antibody analogues". That is, there are a number of modifications that can be made to an antibodies of the invention, including, but not limited to, amino acid modifications in the CDRs (affinity maturation), amino acid modifications in the Fc region, glycosylation variants, and covalent modifications of other types (e.g., for attachment of drug conjugates, etc.).

By "variant" is meant a polypeptide sequence that differs from that of a parent polypeptide by virtue of at least one amino acid modification. In some embodiments, a parent polypeptide is either a full length variable heavy or light chain, listed in SEQ ID NOS: 1 or 2, 13 or 14, or is one or more of the CDR sequences disclosed in any of SEQ ID NOS: 5 to 10, 15 or 16. In some embodiments, an amino acid modification can include a substitution, insertion and/or deletion, with the former being preferred in many cases. In some embodiments, a substitution can be a conservative substitution.

In general, variants can include any number of modifications, as long as the function of the antibody is still present, as described herein. For example, an antibody should still specifically bind to human CRTAM. Similarly, if amino acid variants are generated within the Fc region, for example, the variant antibodies should maintain the required receptor binding functions for the particular application or indication of the antibody. "Variants" of the subject antibodies can be made to have amino acid variations, as described herein, in either one or more of the listed CDR sequences, in one or more of the framework regions, or in one or more of the constant regions (e.g., in the Fc region) of the antibody.

In some embodiments, 1, 2, 3, 4, 5, 6, 7, 8, 9 or 10 amino acid modifications as compared to the parental sequence are generally utilized as often the goal is to alter function with a minimal number of modifications. In some embodiments, there are from 1 to 5 (1, 2, 3, 4 or 5) modifications (e.g., individual amino acid substitutions, insertions and/or deletions), with from 1-2, 1-3 and 1-4 also finding use in many embodiments. For example, in some embodiments, one or more of the CDR sequences of the antibodies of the invention may individually comprise one or more, for example, 1, 2, 3, 4 or 5 amino acid modifications, preferably 1-4, 1-3, 1 or 2 modifications. Generally no more than from 4, 5, 6, 7, 8, 9 or 10 changes are made within a set of CDRs.

It should be noted that the number of amino acid modifications may be within functional domains: for example, it may be desirable to have from 1-5 modifications in the Fc region of a wild-type or engineered protein, as well as from 1 to 5 modifications in the Fv region, for example. A variant polypeptide sequence will preferably possess at least about 75%, 80%, 85%, 90%, 91%, 92%, 93%, 94%, 95%, 96, 97%, 98% or 99% identity to the parent sequences (e.g., the variable region sequences, the constant region sequences, and/or the heavy and light chain sequences and/or the CDRs of, for example, antibody 5A11).

By "amino acid substitution" or "substitution" herein is meant the replacement of an amino acid at a particular position in a parent polypeptide sequence with another amino acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, a parent polypeptide as used herein may refer to 5A11 polypeptides, e.g. the 5A11 $V_H$ or VL chains or the CDR sequences. Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, an anti-CRTAM antibody of the invention is composed of a variant Fc domain. As is known in the art, the Fc region of an antibody interacts with a number of Fc receptors and ligands, imparting an array of important functional capabilities referred to as effector functions. Suitable modifications can be made at one or more positions and in particular for specific amino acid substitutions that decrease or silence binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein. In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In addition, as will be appreciated by those in the art, labels (including fluorescent, enzymatic, magnetic, radioactive, etc., can all be added to the antibodies (as well as the other compositions of the invention).

Bispecific Molecules

In another aspect, the present invention includes bispecific and multispecific molecules comprising an anti-CRTAM antibody, or a fragment thereof, of the invention. An antibody of the invention, or antigen-binding portion thereof, can be derivatized or linked to another functional molecule, e.g. another peptide or protein (e.g., another antibody or ligand for a receptor) to generate a bispecific molecule that binds to two different binding sites or target molecules. In some embodiments, an antibody of the invention, or an antigen-binding portion thereof, can be derivatized or linked to at least two functional molecules, e.g., other peptides or proteins (e.g., other antibodies or ligands for a receptor) to generate a multispecific molecule that binds to at least three different binding sites or target molecules. To create a bispecific or multispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific or multispecific molecule results.

Accordingly, the present invention includes bispecific molecules comprising at least one first binding specificity for a first target epitope (i.e., CRTAM) and a second binding specificity for a second target epitope. The second target epitope may be present on the same target protein as that bound by the first binding specificity; or the second target epitope may be present on a different target protein to that bound by the first binding specificity. The second target epitope may be present on the same cell as the first target epitope (i.e., CRTAM); or the second target epitope may be present on a target which is not displayed by the cell which displays the first target epitope. As used herein, the term "binding specificity" refers to a moiety comprising at least one antibody variable domain.

In another embodiment of the invention, the second target epitope is present on a tumor cell. Therefore, aspects of the invention include bispecific molecules capable of binding both to CRTAM-expressing effector cells (e.g., CRTAM-expressing cytotoxic T cells), and to tumor cells expressing a second target epitope.

In one embodiment, a bispecific antibody of the invention can have a total of either two or three antibody variable domains, wherein a first portion of the bispecific antibody is capable of recruiting the activity of a human immune effector cell by specifically binding to an effector antigen located on the human immune effector cell, in which the effector antigen is CRTAM, said first portion consisting of one antibody variable domain, and a second portion of the bispecific antibody is capable of specifically binding to a target antigen other than the effector antigen, said target antigen being located on a target cell other than said human immune effector cell, and said second portion comprising one or two antibody variable domains.

In an embodiment of the invention in which a binding protein is multispecific, a molecule can further include a third binding specificity, in addition to an anti-tumor binding specificity and an anti-CRTAM binding specificity. In one embodiment, a third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment, or a ligand that binds to a given molecule, e.g., an antigen or a receptor, and thereby results in an enhancement of the effect of the binding determinants for the target cell antigen. The "anti-enhancement factor portion" can bind a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, a bispecific protein of the invention comprises as a binding specificity at least one antibody, or an antigen binding fragment thereof, including, e.g., an Fab, Fab', $F(ab')_2$, Fv, Fd, dAb or a single chain Fv. The antibody may also be a light chain or heavy chain dimer, or any minimal fragment thereof such as an Fv or a single chain construct as described in U.S. Pat. No. 4,946,778, the contents of which is expressly incorporated by reference.

In some embodiments, an antibody that can be employed in a bispecific molecule of the invention is a murine, human, chimeric or humanized monoclonal antibody.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labelled reagent (e.g. an antibody) specific for the complex of interest.

Glycosylation

Another type of covalent modification is alterations in glycosylation. For example, an aglycosylated antibody can be made (i.e., an antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

Another type of covalent modification of the antibody comprises linking the antibody to various non-proteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, for example in the use of the antibodies of the invention for diagnostic or detection purposes, the antibodies may comprise a label. By "labelled" herein is meant that a compound has at least one moiety, element, isotope or chemical compound attached to enable the detection of the compound as described in the 6th Edition of the Molecular Probes Handbook by Richard P. Haugland, hereby expressly incorporated by reference herein.

Methods for Producing the Antibodies of the Invention

The present invention further provides methods for producing the disclosed anti-CRTAM antibodies. These methods encompass culturing a host cell containing isolated nucleic acid(s) encoding an antibody of the invention. As will be appreciated by those in the art, this can be done in a variety of ways, depending on the nature of the antibody. In some embodiments, in the case where the antibodies of the invention are full length traditional antibodies, for example, a host cell contains nucleic acid encoding a heavy chain variable region and a light chain variable region can be cultured under conditions such that an antibody is produced and can be isolated.

The variable heavy and light chains of the antibodies of the invention are disclosed herein (both protein and nucleic acid sequences); as will be appreciated in the art, these can be easily augmented to produce full length heavy and light chains. That is, having provided the DNA fragments encoding $V_H$ and VL segments as outlined herein, these DNA fragments can be further manipulated by standard recombinant DNA techniques, for example, to convert the variable region genes to full-length antibody chain genes, to Fab fragment genes, or to an scFv gene. In these manipulations, a VL- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art (see, e.g., Kabat, E. A., et al. (1991) Sequences of Proteins of Immunological Interest, Fifth Edition, US Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In one preferred embodiment, the heavy chain constant region is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VLregion can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art (see, e.g., Kabat, E. A., et al. (1991) Sequences of Proteins of Immunological Interest, Fifth Edition, US Department of Health and Human Services, NIH Publication No. 91-3242) and DNA fragments encompassing these regions can be obtained by standard PCR amplification. In one preferred embodiment, the light chain constant region is a kappa or lambda constant region.

To create a polynucleotide sequence encoding an scFv antibody fragment, the $V_H$- and VL encoding DNA fragments are operatively linked to another fragment encoding a flexible linker, e.g., encoding the amino acid sequence $(Gly_4\text{-}Ser)_3$, such that the $V_H$ and VL sequences can be expressed as a contiguous single-chain protein, with the VL and $V_H$ regions joined by the flexible linker (see, e.g., Bird et al. (1988) Science 242:423-426; Huston et al. (1988) Proc. Natl. Acad. Sci. USA 85:5879-5883; McCafferty et al., (1990) Nature 348:552-554).

Aspects of the invention include nucleic acids that encode the antibodies of the invention. Such polynucleotides encode for both the variable and constant regions of each of the heavy and light chains, although other combinations are also contemplated by the present invention in accordance with the compositions described herein. Aspects of the invention include oligonucleotide fragments derived from the disclosed polynucleotides and nucleic acid sequences complementary to these polynucleotides.

Polynucleotides in accordance with embodiments of the invention can be in the form of or can include RNA, DNA, cDNA, genomic DNA, nucleic acid analogues, and synthetic DNA. In some embodiments, a DNA molecule may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases, two nucleic acids are used and each is put into a different expression vector (e.g., a heavy chain in a first expression vector, a light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. In some embodiments, a heavy chain and a light chain are produced in the same host cell. In some embodiments, a heavy chain is produced in one host cell and a light chain is produced in another host cell.

Mammalian cell lines available as hosts for expression are known in the art and include many immortalized cell lines available from the American Type Culture Collection (ATCC), Manassas, VA including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Pharmaceutical Compositions

Aspects of the invention include a composition, e.g., a pharmaceutical composition, containing one or more (or a combination of) CRTAM antibodies, or antigen-binding portion(s) thereof, of the present invention, formulated together with a pharmaceutically acceptable carrier. Such compositions may include one or a combination of (e.g., two or more different) antibodies or bispecific molecules of the invention. For example, a pharmaceutical composition of the invention can comprise a combination of antibodies that bind to different epitopes on a target antigen or that have complementary activities.

Pharmaceutical compositions of the invention also can be administered in combination therapy, i.e., combined with other agents. For example, the combination therapy can include an antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or antibody fragment, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains a desired biological activity of the parent compound and does not impart any undesired toxicological effects (see, e.g., Berge, S. M., et al. (1977) J. Pharm. Sci. 66:1-19). A pharmaceutical composition of the invention also may include a pharmaceutically acceptable anti-oxidant. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of an antibody, a dosage can range from about 0.0001 to 100 mg/kg, about 0.001 to 50 mg/kg, about 0.001 to 10 mg/kg, about 0.01 to 10 mg/kg and more usually 0.01 to 5 mg/kg, of the host body weight. For example dosages can be 0.1 mg/kg, 0.2 mg/kg, 0.3 mg/kg, 0.4 mg/kg, 0.5 mg/kg, 0.75 mg/kg body weight, 1 mg/kg body weight, 3 mg/kg body weight, 4 mg/kg body weight, 5 mg/kg body weight, 7.5 mg/kg body weight or 10 mg/kg body weight or within the range of 0.1-5 mg/kg or 1-10 mg/kg. An example treatment regimen entails administration daily, on alternate days, twice per week, once per week, once every two weeks, once every three weeks, once every four weeks, once a month, once every 3 months or once every three to 6 months. Preferred dosage regimens for an anti-CRTAM antibody of the invention include 1 mg/kg body weight, 3 mg/kg, 5 mg/kg or 10 mg/kg body weight via intravenous administration, with the antibody being given using one of the following dosing schedules: (i) every week for six dosages, then every month; (ii) every week; (iii) 3 mg/kg body weight once followed by 1 mg/kg body weight every week.

In some methods, two or more monoclonal antibodies with different binding specificities are administered simultaneously, in which case the dosage of each antibody administered falls within the ranges indicated. In some embodiments, an antibody is administered on multiple occasions. Intervals between single dosages can be, for example, weekly, monthly, every three months or yearly. Intervals can also be irregular as indicated by measuring blood levels of antibody to the target antigen in the patient. In some embodiments, dosage is adjusted to achieve a plasma antibody concentration of about 1-1000 μg/ml and in some methods about 25-300 μg/ml.

In some embodiments, an antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CRTAM antibody of the invention preferably results in a decrease in severity of disease symptoms, an increase in frequency and duration of disease symptom-free periods, or a prevention of impairment or disability due to the disease affliction. For example, a "therapeutically effective dosage" preferably inhibits cell growth or tumor growth by at least about 10%, at least about 20%, at least about 30%, more preferably by at least about 40%, at least about 50%, even more preferably by at least about 60%, at least about 70%, and still more preferably by at least about 80%, at least about 90% or at least about 95% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems (1978) J. R. Robinson, ed., Marcel Dekker, Inc., N.Y.).

In certain embodiments, a monoclonal antibody of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016.); mannosides (Umezawa et al. (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Uses and Methods

The antibodies, antibody compositions and methods of the present invention have numerous in vitro and in vivo diagnostic and therapeutic utilities involving the diagnosis and treatment of immune-mediated disorders.

In some embodiments, these molecules can be administered to cells in culture, in vitro or ex vivo, or to human subjects, e.g., in vivo, to treat, prevent and/or diagnose a variety of disorders. As used herein, the term "subject" is intended to include human and non-human animals. Non-human animals include all vertebrates, e.g., mammals, such as non-human primates, and non-mammals. Preferred subjects include human patients. When antibodies to CRTAM are administered together with another agent, the two can be administered in either order or simultaneously.

Given the specific binding of the antibodies of the invention for CRTAM, the antibodies of the invention can be used to specifically detect CRTAM expression on the surface of immune cells and, moreover, can be used to purify CRTAM via immunoaffinity purification.

Furthermore, given the expression of CRTAM on immune cells, the antibodies, antibody compositions and methods of the present invention can be used to treat a subject with a tumorigenic disorder, e.g., a disorder characterized by the presence of tumor cells, for example small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In one embodiment, antibodies of the present invention are used for the treatment of cancer, for example, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In a further embodiment, the antibodies of the invention are used in the manufacture of a medicament for the treatment of cancer, for example, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In one embodiment, the antibodies (e.g., monoclonal antibodies, antibody fragments, Nanobodies, multispecific and bispecific molecules and compositions, etc.) of the invention can be used to detect levels of CRTAM, or levels of immune cells which contain CRTAM on their membrane surface, which levels can then be linked to certain disease symptoms for diagnosis.

In another embodiment, the antibodies (e.g., monoclonal antibodies, multispecific and bispecific molecules and compositions) of the invention can be initially tested for binding activity associated with therapeutic or diagnostic use in vitro. For example, compositions of the invention can be tested using the flow cytometric assays described in the examples below.

In some embodiments, the antibodies (e.g., monoclonal antibodies, multispecific and bispecific molecules and compositions) of the invention have additional utility in therapy and diagnosis of diseases. For example, the monoclonal antibodies, the multispecific or bispecific molecules can be used to elicit in vivo or in vitro one or more of the following biological activities: to induce and/or enhance activation of an immune cell; to mediate phagocytosis or ADCC of a cell in the presence of human effector cells expressing CRTAM, or to block an CRTAM ligand from binding to CRTAM.

In a particular embodiment, the antibodies (e.g., monoclonal antibodies, multispecific and bispecific molecules and compositions) are used in vivo to treat, prevent or diagnose a variety of diseases. Examples of relevant diseases include, among others, human cancer tissues representing small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

Suitable routes of administering the antibody compositions (e.g., monoclonal antibodies, multispecific and bispecific molecules and compositions) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, the anti-CRTAM antibodies of the invention can be co-administered with one or more additional therapeutic agents, e.g., an immunostimulatory agent, a cytotoxic agent, a radiotoxic agent or an immunosuppressive agent. An antibody can be linked to an agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation therapy. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Other agents suitable for co-administration with the antibodies of the invention include other agents used for the treatment of cancers, such as Avastin®, 5FU and gemcitabine. Co-administration of the anti-CRTAM antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells.

Target-specific effector cells, e.g., effector cells linked to compositions (e.g., monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose.

Therapy with target-specific effector cells can be performed in conjunction with other techniques. For example, anti-tumor therapy using the compositions (e.g., monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

Aspects of the invention include kits comprising the antibody compositions of the invention (e.g., monoclonal antibodies, bispecific or multispecific molecules) and instructions for their use, e.g., in the treatment of cancer. The kit can further contain one or more additional reagents, such as an immunosuppressive reagent, a cytotoxic agent or a radiotoxic agent, or one or more additional antibodies of the invention (e.g., an antibody having a complementary activity which binds to an epitope in the CRTAM antigen distinct from the first antibody).

Accordingly, patients treated with antibody compositions of the invention can be additionally administered (prior to, simultaneously with, or following administration of an antibody of the invention) another therapeutic agent, such as a cytotoxic or radiotoxic agent, which enhances or augments the therapeutic effect of the antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include granulocyte colony-stimulating factor (G-CSF), granulocyte-macrophage colony-stimulating factor (GM-CSF), interferon-γ (IFN-γ), and tumor necrosis factor (TNF).

The compositions (e.g., antibodies, multispecific and bispecific molecules) of the invention can also be used to target cells expressing FcγR or CRTAM, for example, for labelling such cells. For such use, the binding agent can be linked to a molecule that can be detected. Thus, the invention provides methods for localizing ex vivo or in vitro cells expressing Fc receptors, such as FcγR, or CRTAM. The detectable label can be, e.g., a radioisotope, a fluorescent compound, an enzyme, or an enzyme co-factor.

In a particular embodiment, the invention provides methods for detecting the presence of the CRTAM antigen in a sample, or measuring the amount of the CRTAM antigen, comprising contacting the sample, and a control sample, with a monoclonal antibody, or an antigen-binding portion thereof, which specifically binds to CRTAM, under conditions that allow for formation of a complex between the antibody or portion thereof and CRTAM. The formation of a complex is then detected, wherein a difference in complex formation between the sample compared to the control sample is indicative of the presence of the CRTAM antigen in the sample.

In other embodiments, the invention provides methods for treating an immune-mediated disorder in a subject, e.g., human cancers, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependent claims.

The present invention is further illustrated by the following examples which should not be construed as further limiting. The following examples, sequences and figures are provided to aid the understanding of the present invention, the true scope of which is set forth in the appended claims. It is understood that modifications can be made in the procedures set forth without departing from the spirit of the invention.

EXAMPLES

Example 1: Antibody Generation and Screening

Hybridoma Generation

Rat monoclonal anti CRTAM antibodies were generated by genetic immunization. CRTAM ECD (SEQ ID NO: 12) was used to create a plasmid pB8-CRTAM-hum.ECD (Aldevron, Freiburg) for immunization. Plasmid pB8-CRTAM-hum.ECD was used to immunize three rats. Splenocytes from immunized rats were fused with a myeloma cell line to generate hybridomas using industry standard techniques.

Rat Immunization and Titer Test

Animals were immunised with the vector (pB8-CRTAM-hum.ECD). For detection of the presence of target specific antibodies ("antibody titer") in the serum of the immunized animals a flow cytometry-based assay (FACS test) was performed.

Hybridoma Screen

A FACS assay was used to identify overexpressing hybridoma cells. One hundred and eight hybridoma clones were identified as positive from primary screen.

Secondary Screen

Recombinant hCRTAM/Fc Chimera (R&D Systems, Catalogue 1695-CR) were coated at 100 ng/well onto high binding assay plates (Cat No 12-565-136, Thermo Scientific) diluted in 1× Dulbecco's phosphate-buffered saline (DPBS) (Cat No SH30028-03, Thermo Scientific). The plates were washed three times with wash buffer, 1×DPBS and 0.05% Tween 20 (Cat No BP337-500, Fisher Scientific) using Tecan Hydro speed 96-well plate washer.

The antigen coated plates were blocked with a solution of superblock (available from Thermo fisher) solution for 1 hr at room temperature (RT) after washing. 100 μl of hybridoma supernatant, 1:5 diluted in ELISA buffer (ELISA buffer, 1×DPBS, 0.05% Tween 20, and 1% Bovine Serum Albumin, Cat No SH30574.02, Thermo Scientific) was added to each well. Following primary antibody incubation plates were washed three times with wash buffer. An HRP conjugated secondary antibody, goat anti-rat IgG diluted 1:5000 in ELISA buffer (H&L chain-specific Jackson Immunoresearch, catalog number 112-035-167) was added to the plates for an hour at RT. The plate was washed three times in wash buffer. 1-Step Ultra TMB-ELISA (Cat No 34028, Thermo Scientific) was added to each well to develop a detectable signal. After the signal was fully developed, 2N sulfuric acid (Cat No 8140-16, Ricca Chemical Company) was added to all wells to stop the reaction. Optical Density (OD) of each sample was determined using VERSA max microplate reader at 450 nm wavelength.

Example 2: Structural Characterization of Monoclonal Antibodies to CRTAM

The cDNA sequences encoding the heavy and light chain variable regions of the monoclonal antibodies were obtained using standard PCR techniques and were sequenced using standard DNA sequencing techniques. The heavy and light chain variable regions of 5A11 selected from the screen can be seen in FIG. 1.

The nucleotide and amino acid sequences of the heavy chain variable region of 5A11 are shown in SEQ ID NO: 3 and 1, respectively.

The nucleotide and amino acid sequences of the light chain variable region of 5A11 are shown in SEQ ID NO: 4 and 2, respectively.

Further analysis of the 5A11 VH sequence using the Kabat system of CDR region determination led to the delineation of the heavy chain CDR1, CDR2 and CDR3 regions as shown in SEQ ID NOs: 5, 6 and 7, respectively. FIG. 1*a* shows 5A11 VH sequences with CDR1, CDR2 and CDR3 boxed.

Further analysis of the 5A11 VL sequence using the Kabat system of CDR region determination led to the delineation of the light chain CDR1, CDR2 and CDR3 regions as shown in SEQ ID NOs: 8, 9 and 10, respectively. FIG. 1*b* shows 5A11 VL sequences with CDR1, CDR2 and CDR3 boxed.

Example 3: Specificity of Monoclonal Antibodies to CRTAM Determined by Flow Cytometry Analysis Preparation of In Vitro Activated T Cells Peripheral blood mononuclear cells (PBMCs) were isolated from human buffy coat as described above. 2 E6 cells/ml PBMC were cultured in T cell culture medium (AIM V medium with 5% FBS, Cat #SH3008703, Fisher, Pittsburgh, PA) and 300 u IL2 (Cat #200-02, Peprotech, Rocky Hill, NJ) in the presence of 100 ng/ml anti-CD3 (OKT3) for 4 days. Following this the cells were cultured with anti-CD3/anti-CD28 activation beads (Cat #11132D, Thermo Fisher, Waltham, MA) for 24 hours before FACS analysis (data not shown).

Enzyme-Linked Immunosorbent Assay (ELISA)

Fluorescence-activated cell sorting (FACS) analysis was performed in 96-well plate format according to standard protocols. Activated T cells were prepared as above. All subsequent steps of the staining protocol were carried out on ice with ice-cold reagents except for the centrifugation steps which was done at RT. Three-fold serial dilutions of the antibodies, were prepared in FACS buffer to give a 12-point titration curve with final concentrations ranging from 133 nM to 1 pM. The corresponding hybridoma supernatants, isotype controls, and positive control antibodies were diluted in ice cold FACS buffer to be tested at a single point with a final concentration of 30 nM. The antibody dilutions were each dispensed (100 μL/well) into one well for each cell line. One well was left unstained in FACS buffer. Following 30 minutes incubation with primary antibody or control, cells were washed twice by addition of FACS buffer followed by centrifugation for 5 minutes at 1200 rpm. The supernatant was discarded and the cell pellets were retained. The secondary antibody, goat anti-rat-IgG (H+L)-RPE was diluted to a working concentration of 1 μg/mL and applied to all wells except one of the wells unstained with primary antibody. Secondary antibody was incubated with the cells for 30 minutes. Cells were washed twice by addition of FACS buffer followed by centrifugation for 5 minutes at 1200 rpm. The final cell pellets were re-suspended in 150 μL FACS buffer+50 μl of 4% paraformaldehyde and fixed until ready to be acquired in a Flow cytometer. The plates were left at 4° C. until acquisition. Geometric mean fluorescence intensity (GMFI or Geo Mean) of each sample was determined using a Guava Easycyte Plus high-throughput flow cytometer (96 well plates) and raw data were analyzed using the Guava Cytosoft Pro Software Module, version 2.2.2 (Millipore, Billerica MA). Geo Mean was plotted versus antibody concentration and GraphPad™ Prism software was used to perform nonlinear regression, sigmoidal dose-response analysis and calculate EC50 for antibody binding on activated T cells. FIG. 3 shows 5A11 specific dose-related binding to activated T cells as compared to the commercially available anti-CRTAM antibody CR24.1 (BioLegend). As can be seen antibody 5A11 shows superior binding to activated T cells.

Example 4: Cross-Reactivity of Anti-CRTAM Antibodies

Enzyme-Linked Immunosorbent Assay (ELISA)

Enzyme-Linked Immunosorbent Assay (ELISA) analysis was performed in 96-well plate format according to standard protocols. 96-well ELISA plate (Cat No 12-565-136, Thermo Scientific) was coated overnight at 4° C. with 100 μl of 1 μg/mL cyno CRTAM HIgG1-Fc proteins in 1×Dulbecco's phosphate-buffered saline (DPBS) (Cat No SH30028-03, Thermo Scientific). The plate was washed three times with wash buffer, 1×DPBS and 0.05% Tween 20 (Cat No BP337-500, Fisher Scientific), blocked with 250 μl of superblock buffer (Cat No 37515, Thermo Scientific) for 30 minutes at RT, then washed again three times with wash buffer.

The anti-CRTAM antibodies were serially diluted 1:3 in ELISA buffer, 1×DPBS, 0.05% Tween 20, and 1% Bovine Serum Albumin (Cat No SH30574.02, Thermo Scientific), to obtain an 8-point titration curve with final concentration ranging from 0.003 to 2 μg/ml and applied to the wells in duplicate. The last well was left as blank in ELISA buffer. Following 60 minutes incubation with primary antibody, the plate was washed three times in wash buffer. The secondary antibody, Peroxidase-conjugated AffiniPure Goat-anti-Rat IgG (H+L) was diluted 1:5000 in ELISA buffer and was applied to the wells with the CRTAM antibodies and Isotype control for 60 minutes. Peroxidase conjugated AffiniPure F(ab')2 Fragment Goat anti Mouse IgG (H+L) was also diluted in 1:5000 in ELISA buffer and was applied to the wells with CR24.1 for 60 minutes.

The plate was washed three times in wash buffer. 1-Step Ultra TMB-ELISA (Cat No 34028, Thermo Scientific) was added to each well to develop a detectable signal. After the signal was fully developed, 2N sulfuric acid (Cat No 8140-16, Ricca Chemical Company) was added to all wells to stop the reaction. Optical Density (OD) of each sample was determined using VERSA max microplate reader at 450 nm wavelength. Absorbance for each sample was averaged from duplicate wells, plotted versus antibody concentration, and EC50 was calculated using nonlinear regression and sigmoidal dose-response analysis.

The anti-CRTAM antibody 5A11 demonstrated binding to the cynomolgus CRTAM protein in a dose-dependent manner, while CR24.1 was found not to bind to the cynomolgus CRTAM protein. FIG. 4 shows the cross-reactivity of 5A11.

Example 5: Ability of Anti-CRTAM Antibodies to Activate T Cells and Stimulate IFNγ Production Preparation of in vitro activated T cells by anti-CRTAM and anti-CD3 antibodies 96-well non-tissue culture plates were coated with 2 μg/ml OKT3 and different concentrations of anti-CRTAM antibodies/isotypes (titrated from 20 μg/ml with 1:2 dilution 11 times) at 4° C. overnight. The plates were washed with PBS twice, followed by blocking with AIMV plus 5% FBS for 30 min. After blocking, 0.1 million OKT3-primed T cells (Day 4), produced as described in Example 3, were resuspended into fresh AIMV medium and added onto the plates. After one day incubation at 37° C. the supernatants were collected and diluted for use in an IFNγ ELISA assay.

Enzyme-Linked Immunosorbent Assay (ELISA) for IFNγ Determination

IFNγ was measured with the corresponding Ready-SET-Go! ELISA kit from eBiosciences (Cat. #50-173-24 Fischer Scientific). Following the manufacturer's instructions, the high-binding plate (Corning 3690) was coated with capture antibody (1:250 diluted in coating buffer) overnight at 4° C., then washed with wash buffer (PBS+0.05% Tween-20) three times. The plate was blocked with Assay Diluent for 1 hour on a shaker. The cell culture supernatant was added to the plates at appropriate dilution (1:400 for IFNγ), and incubated for 2 hours on a shaker followed by 3 times wash. Biotinylated detection antibodies (provided in the kit) diluted 1:250 in Assay Diluent were added and incubated for 1 hour on a plate shaker. The plate was washed with wash buffer and a HRP conjugated Streptavidin (provided in the kit) diluted 1:1000 in Assay Diluent was added. After 30 minutes of incubation on a plate shaker, the plate was washed and TMB substrate solution (provided in the kit) was added. The development reaction was stopped after approximately 5-10 minutes with the addition of 2N $H_2SO_4$ solution and the absorption was read on a plate reader at 450 nm (OD450).

Results

Figure 5:
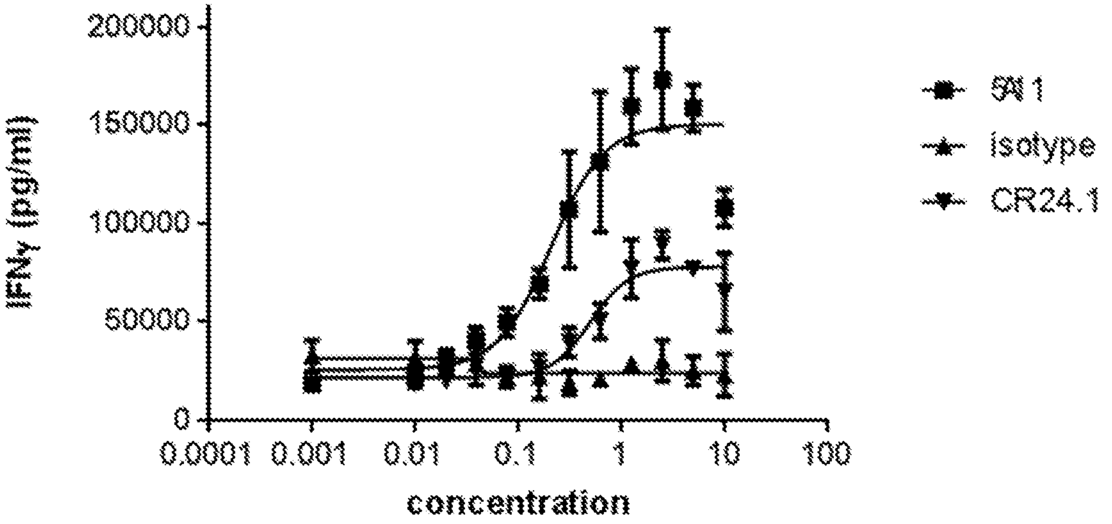
FIG. 5 shows the enhanced ability of antibody 5A11 to mediate IFNγ production compared to CR24.1 upon T cell activation.

5A11 antibody showed enhanced activity in the OKT3 pre-activated T cells reflected in increased IFNγ production when compared to antibody CR24.1 (FIG. 5). This shows that antibodies directed toward CRTAM will have therapeutic effect in patients with inhibited immune systems.

Example 6: Humanisation of Antibody 5A11

The humanization of rat 5A11 monoclonal antibody was performed using CDR-grafting technology. To guide the humanization process and help in the decision to conserve parental rat residues or substitute them with their human germline counterparts a homology molecular model of the Fv of 5A11 rat monoclonal antibody was built.

The definition of the CDRs is based on the Kabat nomenclature. The selection of human framework acceptor regions into which 5A11 rat CDR regions are grafted was accomplished by searching the IMGT rat and human V genes database using IgBLAST, developed at NCBI to facilitate analysis of immunoglobulin V region sequences, with 5A11 rat variable region sequences as input. The applied strategy was to use the human germline sequences that are natural human sequences not containing the idiosyncratic somatic mutations found in individual human antibody sequences.

Homology Molecular Model of the 5A11 Rat Antibody

Methodology of Homology Model Building

A model of the antibody BUH-5A11-F2 ('5A11') was constructed according to established protocols (Ramos O H P. Computer-assisted modeling of antibody variable domains. Methods Mol Biol 2012; 907: 39-55). The variable heavy (VH) and light (VL) chain sequences were separately numbered/annotated according to the IMGT convention in order to separate the framework and CDR sequences.

The VL framework residues were used to search the sequences of solved antibody structures via protein BLAST.

The top hit was provided by the VL of the structure of 4AIZ (1.75 A resolution) (65 of 108 identical residues). This was selected as the template, however the slightly lower ranked hit provided by the VL of structure 3G6D (3.20 A resolution) (64 of 107 identical residues) was employed to fix the conformation of the N-terminal serine missing from 4AIZ. The VL CDR2 sequence was an identical match to that of 4AIZ; thus there was no need to search for a CDR2 template. The sequences of VL CDR1 and CDR3, with the addition of two residues on each end, were used to search the sequences of solved antibody structures via protein BLAST. The top hit for VL CDR3 was the structure 1NFD (2.80 A resolution) (11 of 15 identical residues). No murine or rat antibody structures match the sequence of CDR1 with the addition of two residues on each end; searching for murine or rat antibody structures with the VL framework also yield no good approximate hits. The best match for CDR1, searching across human structures returned the human V-lambda in 4AIZ (5 of 10 identical residues) used as the VL template. PyMol (PyMOL Molecular Graphics System, Version 1.3r1, Schrodinger, LLC.) was used to fit the CDR3 template to the framework template using the two residue overhangs on the ends to anchor the CDR template fragment to the VL framework template. The assembled VL partial model was manually subjected to mutagenesis (in PyMol), with selection of optimal rotamers, in order to match the 5A11 VL sequence.

The VH framework residues were used to search the sequences of solved antibody structures via protein BLAST. The top hit was provided by the VH of the rat antibody structure 5AUM (2.05 A resolution) (85 of 116 identical residues); this antibody is of the same IGHV10-5 germline as 5A11 and was thus selected as template. The sequences of VH CDR1, CDR2, and CDR3, with the addition of two residues on each end, were used to search the sequences of solved antibody structures via protein BLAST. The top hit for VH CDR1 was provided by the structure of 4HPY (1.50 A resolution) (9 of 11 identical residues). The top hit for VH CDR2 was provided by the structure of 5AUM (11 of 14 identical residues). The top hit for VH CDR3, 1Q72, was not selected as template because of the presence of 4 gaps in the alignment; instead, the lower ranked hit structure 4BZ1 (1.50 A resolution) (7 of 14 identical residues) was selected; this was because an overlap of the 1Q72 and 4BZ1 CDR3 fragments shows that the N and C-terminal sections match well with the framework template and each other, while 4BZ1 provides satisfactory closure of the sequence insertion found in 1Q72. The CDR templates were fitted to the framework template (in PyMol) using the two residue overhangs on the ends to anchor each CDR template fragment to the framework template. Finally, the assembled VH partial model was manually subjected to mutagenesis (in PyMol), with selection of optimal rotamers, in order to match the 5A11 VH sequence. Subsequently, the best tertiary arrangement of the VH and VL partial models was selected in order to assemble the final model. The VH and VL template sequences were submitted to the PAPS (Packing Angle Prediction Server—Abhinandan K R, Martin A C R. Analysis and prediction of vh/vl packing in antibodies. Protein Eng Des Sel 2010; 23: 689-697) in order to find a predicted best-fit tertiary arrangement. The PAPS server predicted that the solved antibody structure 1D5B, with a relative packing angle of −44.5 degrees, would provide the best tertiary arrangement of VH and VL. Thus, the final model was assembled by fitting the backbone coordinates of the conserved anchor segments (residues 41-44 and 101-104) of the VH and VL partial models to 1D5B (in PyMol). Lastly, the coordinates of this final model were subjected to a round of energy minimization employing GROMACS (Van Der Spoel D, Lindahl E, Hess B, Groenhof G, Mark A E, Berendsen H J C. Gromacs: fast, flexible, and free. J Comput Chem 2005; 26: 1701-1718) with the GROMOS96 (Scott W R P, Hunenberger P H, Tironi I G, Mark A E, Billeter S R, Fennen J, Torda A E, Huber T, Kruger P, van Gunsteren W F. The gromos biomolecular simulation program package. J Phys Chem A 1999; 103: 3596-3607) force-field.

Heavy Chain Design

Amino Acid Differences with Most Homologous Rat Germline, IGHV10-5*01

Amino acid sequence of the VH (SEQ ID NO:1) isolated from the rat 5A11 hybridoma (CDR regions according to the Kabat numbering scheme are in bold).

```
FR1                                        CDR1      FR2
AVQLVESGGGLVQPKESLKISCAASGFTFSDAAMYWVRQAPGKGLEWVA

   CDR2                                    FR3
RIRTKTNNYAAHYVESVKGRFTVSRDDSKSMVYLQMDNLKTDDTAMYYC

      CDR3        FR4
TSVPQGTQDYWGQGVMVTVSS
```

91% identity (91 identical residues out of a total of 100 amino acids) between the 5A11 rat heavy chain variable (VH) region (SEQ ID NO: 1) and the rat germline immunoglobulin VH 10-5*01 (IGHV10-5*01) (amino acids 1-100 of SEQ ID NO:1).

```
                 <-------------FR1------------><CDR><-----FR2---->
5A11 VH       1  AVQLVESGGGLVQPKESLKISCAASGFTFSDAAMYWVRQAPGKGLEWVA      49

IGHV10-5*01  1  ..............................N..................      49

                 <-------CDR2------><--------------FR3------------->
5A11 VH      50 RIRTKTNNYAAHYVESVKGRFTVSRDDSKSMVYLQMDNLKTDDTAMYYCTS    100

IGHV10-5*01 50  .....P....TY.AD.......I..................E........A    100
```

Selection of Human Framework Acceptor VH Regions

The selection of human framework acceptor VH regions into which the 5A11 rat CDR regions are grafted was accomplished by searching the IMGT human VH gene database using IgBLAST with the rat VH region amino acid sequence as input. Based on the sequence alignment of the Parental antibody to the human germlines, the closest matching entries were identified. The identification of the optimal human germline as acceptor was based on the following ordered criteria: sequence identity across the framework as defined by Kabat, and identity and/or compatibility of inter-chain interface residues and support loops with the canonical conformations of the Parental CDRs. From this analysis, the human germline IGHV3-73*01 appeared to be the best choice as human framework acceptor regions, with an overall percentage of identity of 75% (75 residues out of a total of 100). Thus, this human germline was used for the design of the humanized version. Rat germline J2 gene (IGHJ2*01) was identified as the segment gene most homologous to the corresponding rat 5A11 VH J gene. In FR4, the sequence of the 5A11 VH is identical to that of rat IGHJ2*01 germline gene. The rat J2-segment gene was compared to the human J-segment genes over CDR3 and FR4, and the human J segment IGHJ4 (IGHJ4*01) was selected.

Design Using IGHV3-73*01 Human Germline as Framework Acceptor Regions Humanized Version a (Amino Acids 1-100 of SEQ ID NO: 13)

Rat CDRs (bold) as defined by the Kabat nomenclature were grafted into IGHV3-73*01 to obtain the hereunder detailed sequence. Residues underlined are framework rat residues (outside CDR residues) i.e. conserved from the Parental rat 5A11 VH sequence (SEQ ID NO:1); they have been conserved because they might be structurally important for maintaining the full activity of the antibody.

```
Version A (aa 1-100 of SEQ ID NO: 13 -
5A11-373-VHA)
     FR1                           CDR1     FR2
EVQLVESGGGLVQPGGSLKLSCAASGFTFSDAAMYWVRQASGKGLEWVA

   CDR2                               FR3
RIRTKTNNYAAHYVESVKGRFTVSRDDSKNTVYLQMNSLKTEDTAMYYC

TS
```

85% identity (85/100) of humanized version A with IGHV3-73*01 human germline (aa 1-100 of SEQ ID NO: 13-5A11-373-VHA)

```
                       <-------------FR1------------><CDR><-----FR2---->
5A11-373-VHA      1    EVQLVESGGGLVQPGGSLKLSCAASGFTFSDAAMYWVRQASGKGLEWVA      49

IGHV3-73*01       1    .............................GS..H..............G      49

                       <------CDR2-------><--------------FR3------------->
5A11-373-VHA     50    RIRTKTNNYAAHYVESVKGRFTVSRDDSKNTVYLQMNSLKTEDTAMYYCTS   100

IGHV3-73*01      50    ...S.A.S..TA.AA.......I........A.............V....R   100
```

In framework 2 (FR2), Kabat residue H49 Ala is known as a "Vernier residue"; it is adjacent to VH-CDR2 and can affect CDR conformations and fine-tuning of antigen recognition. In framework 3 (FR3), Kabat residues H69 Val and H78 Val are known as "Vernier residues". They are adjacent to the CDRs and can affect CDR conformations and fine-tuning of antigen recognition.

Light Chain Design

Amino Acid Differences with Most Homologous Rat Germline, IGLV4-S1*01

```
Amino acid sequence of rat 5A11 VL (SEQ ID NO: 2)
(CDR regions highlighted)
FR1                        CDR1             FR2
SYELIQPPSASVTLGNTVSLTCVGDELSKRYVQWSQQKPDKTIVSVIY

CDR2                FR3                              CDR3
KDSERPSGISDRFSGSSSGTTATLTIHGTLAEDEADYYCLSTYSDDNL

     FR4
PVFGGGTKLTVL
```

97.9% (94/96) identity (94 identical residues out of a total of 96 amino acids) between the 5A11 rat VL and the rat germline immunoglobulin lambda variable IGLV4-S1*01. (amino acids 1-96 of SEQ ID NO: 2)

```
                       <---------FR1--------><--CDR1---><-----FR2----->
5A11 VL          1     SYELIQPPSASVTLGNTVSLTCVGDELSKRYVQWSQQKPDKTIVSVIY      48

IGLV4-S1*01      1     ..............................A..Y.............      48

                       <CDR2-><--------------FR3-------------><--CDR3--      96
5A11 VL          49    KDSERPSGISDRFSGSSSGTTATLTIHGTLAEDEADYYCLSTYSDDNL      96

IGLV4-S1*01      49    ................................................      96
```

Selection of Human Framework Acceptor VL Regions

The selection of human framework acceptor VL regions into which the 5A11 VL rat CDR regions are grafted was accomplished by searching the IMGT human VL genes database using IgBLAST with the rat VL region amino acid sequence as input. Based on the sequence alignment of the Parental antibody to the human germlines, the closest matching entries were identified. The identification of the optimal human germline as acceptor was based on the following ordered criteria: sequence identity across the framework as defined by Kabat, and identity and/or compatibility of inter-chain interface residues and support loops with the canonical conformations of the Parental CDRs. From this analysis, human germline, IGLV3-27*01, appeared to be the best choice as human framework acceptor regions with an overall percentage of identity of 64.6% (62 amino acid residues out of a total of 96). Thus, this human germline was used for the design of the humanized versions.

Rat germline J1 gene (IGKJ1*01) was identified as the gene segment most homologous to the corresponding rat 5A11 VL J gene the ). The rat J1-gene segment was compared to the human J-segment genes over CDR3 and FR4, and the human J-segment IGKJ2 (IGKJ2*01) was found to have the highest overall homology.

Design Using IGLV3-27*01 Human Germline as Framework Acceptor Regions Humanized Version Rat CDRs as defined by the Kabat numbering were grafted into IGLV3-27*01 to obtain the hereunder detailed sequence. A number of rat framework residues structurally important for maintaining the full activity of the antibody have been retained. This gave a humanized version with 87.5% identity (84 amino acid residues out of 96) to IGLV3-27*01 human germline (amino acids 1-96 of SEQ ID NO: 14).

```
                  <---------FR1-------><--CDR1---><-----FR2----->
5A11-327-VLC      SYELTQPSSVSVSPGQTARITCSGDVLSKRYAQWSQQKPGQAIVSVIY

                  <CDR2-><-------------FR3------------><--CDR3--
5A11-327-VLC      KDSERPSGIPERFSGSSSGTTATLTISGAQVEDEADYYCLSTYADDNL

(aa 1-96 of SEQ ID NO: 14(5A11-327-VLC)
                  <---------FR1-------><--CDR1---><-----FR2----->
5A11-327-VLC      SYELTQPSSVSVSPGQTARITCSGDVLSKRYAQWSQQKPGQAIVSVIY
IGLV3-27*01       ...........................A.K..R.F......P.L....

                  <CDR2-><-------------FR3------------><--CDR3--
5A11-327-VLC      KDSERPSGIPERFSGSSSGTTATLTISGAQVEDEADYYCLSTYADDNL
IGLV3-27*01       .....................V.................Y.A-..N.-
```

Example 7 Perforin/Granzyme Assay

Figure 7:
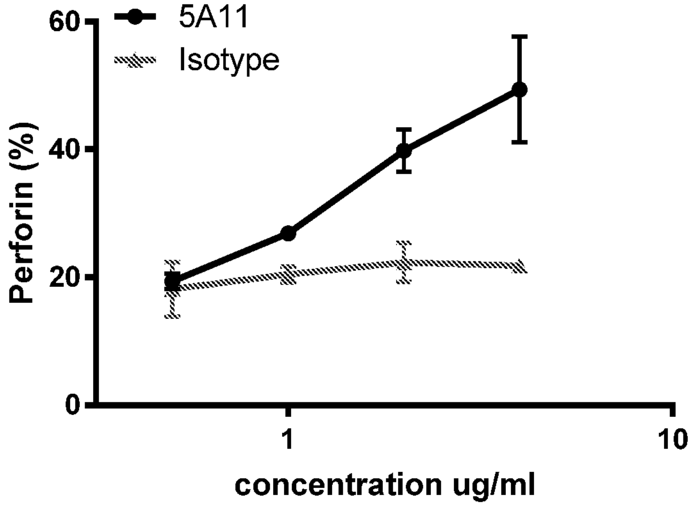
FIG. 7 shows that antibody 5A11 can activate T-cells in vitro to produce perforin in a dose dependent manner.
Figure 8:
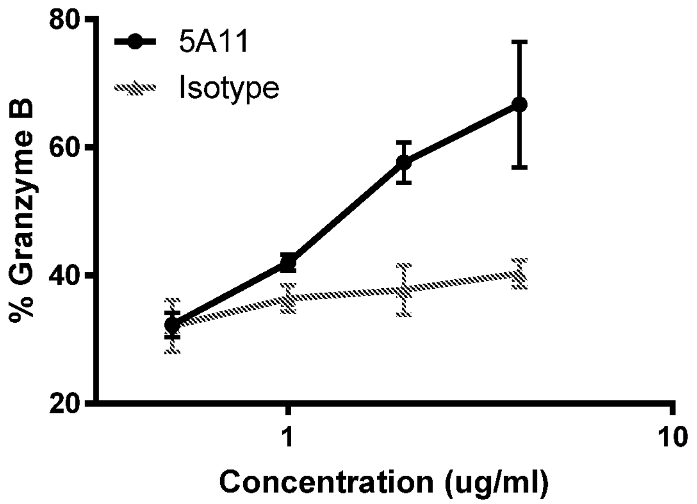
FIG. 8 shows that antibody 5A11 can activate T-cells in vitro to produce granzyme B in a dose dependent manner.

Cytotoxic potential induced by anti CRTAM antibodies was assessed by measuring perforin and granzyme B production by CD8+ cytotoxic lymphocytes following stimulation. Human CD8 T cells were negatively isolated from healthy donor PBMCs with commercially available kit (Miltenyi Biotec). Isolated CD8 cells were stimulated with plate-bound CD3 (OKT3, 0.1 μg/ml) and different doses of 5A11 for 4 days. Following on-plate stimulation, CD8 cells were treated with PMA (25 ng/ml), lonomycin (10 μg/ml) and brefeldin (10 μg/ml) for 4 h. Cells were then washed, fixed with 4% PFA for 10 min and stained with perforin and granzyme B antibodies for flow cytometry diluted in PBS containing 0.5% saponin for 15 min. After staining cells were washed 2× in PBS containing 0.5% saponin and 1× in FACS buffer (PBS containing 2% FCS and 2 mM EDTA). Washed cells were resuspended in FACS buffer and analysed using Attune NxT (Fisher Scientific) flow cytometer. As detailed in FIG. 7 and FIG. 8, stimulation with increasing doses of 5A11 increased the cytotoxic potential of CD8 T cells in a dose-dependent manner.

Example 8 T-cell Cytotoxicity Assay

T-cell cytotoxicity against MCF-7 breast cancer cells using anti-CRTAM antibodies was assessed using Her2/CD3 bispecific antibody as an anchor for T cells and MCF-7 cells. Additional cytotoxicity was observed when anti-CRTAM antibodies were added to the assay wells containing tumor cells, PBMCs and Her2/CD3 bispecific antibody. The percentage of cytotoxicity associated with the action of the anti-CRTAM antibody was calculated as percent killing when compared to cells not treated with anti-CRTAM antibodies.

Freshly Isolated PBMCs were harvested by centrifugation for 5 minutes at 1000×g and diluted in DMEM complete medium to 1.5 $E^6$ cells/ml. PBMCs were aliquoted and test antibodies added (5A11 antibody) to 20 μg/ml. The cells were incubated on ice 10-20 mins. MCF-7 cells were collected and diluted to a density of 1.5 $E^6$ cells/ml.

50 ul of the resulting cell suspensions of both PBMCs and MCF-7 were added to each well such that each well contained 75 000 PBMCs and MCF-7 cells. Her2/CD3 bispecific antibody was serially diluted in complete DMEM media and 10 ul of this dilution was added to each well to produce 5 μg/ml final dilution in each assay well.

Untreated wells with 50 ul/well of culture medium represented negative controls. Assay plates were incubated for 96 hours at 37° C. with 5% $CO_2$. Following incubation, assay plates were equilibrated to RT for 30 minutes. PBMCs were removed and discarded leaving MCF-7 cells in the assay wells. The plates were washed thrice with PBS at RT and 100 ul RT PBS was added to each well. Cell Titer-Glo® reagent (Cat. No. G7572, Promega, Madison, WI) was prepared according to manufacturer directions and dispensed 100 ul/well. The reagent was pipetted in and out of assay wells several times to mix and induce cell lysis. The assay plate was incubated 15 minutes in the dark. Luminescence was recorded using a GloMax® luminometer (Promega) according to manufacturer recommendations.

The viable cell count was proportional to luminescence units and the mean was calculated for each concentration in assayed wells. Percent viability was calculated using wells without the Test antibody as the control and was plotted versus antibody concentration.

Figure 9:
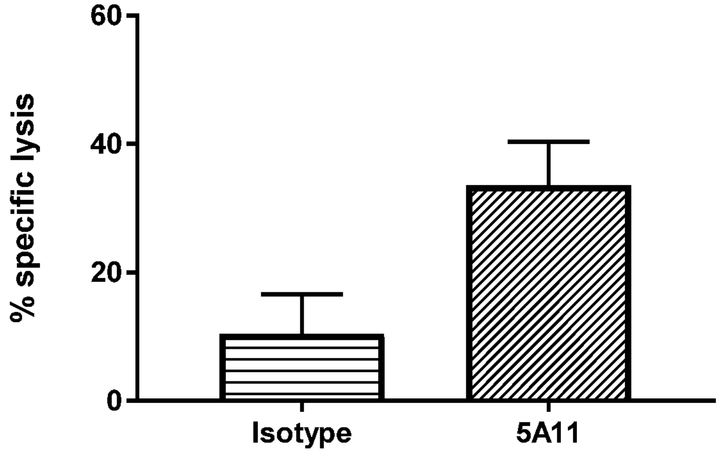
FIG. 9 shows that antibody 5A11 can induce in vitro T cell mediated cytotoxicity in MCF7 tumor cells.

As can be seen from FIG. 9 the addition of antibody 5A11 significantly increased the level of cytotoxicity compared to the control without 5A11 antibody.

Example 9 ELISPOT with Tumor Infiltrating Lymphocytes

Figure 10:
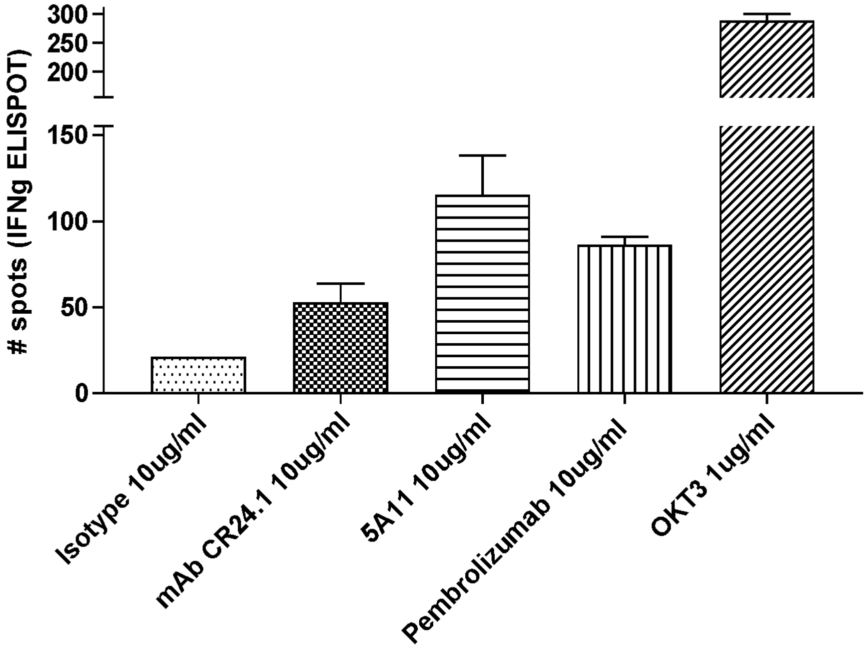
FIG. 10 shows that antibody 5A11 can induce tumor infiltrating lymphocytes (TILs) isolated from primary NSCLC tumor samples to produce interferon gamma in ex vivo assays. This assay shows that antibody 5A11 has enhanced activity when compared to commercially available antibody CR24.1

Primary tumor-derived tumor infiltrating lymphocytes (TILs) from NSCLC (FIG. 10) or Breast cancer (FIG. 11) tumors were stimulated for 96 h with CR24.1, 5A11 or pembrolizumab diluted to the indicated concentrations and OKT3 diluted to 1 μg/ml in complete RPMI culture media. After stimulation TILs were harvested, counted and plated on IFNγ ELISPOT plate (Mabtech) at 100 000 cells/well. The plate was incubated at 37° C. for 24 hours and subsequently developed according to the manufacturer's instructions. The number of spots was read using ImmunoSpot® Series 5 ELISPOT analyser the data was analysed using GraphPad Prism software. FIG. 10 shows that antibody 5A11 activates a greater number of NSCLC derived TILs reflecting a significantly higher IFNγ production than either the commercial antibody CR24.1 or pembrolizumab.

Figure 11:
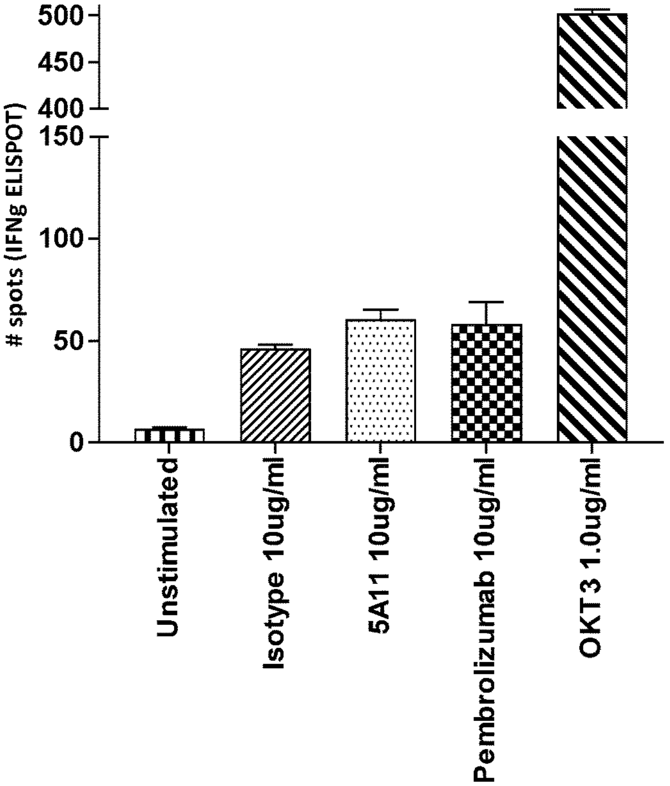
FIG. 11 shows that antibody 5A11 can induce TILs isolated from primary breast cancer samples to produce interferon gamma in ex vivo assays.

FIG. 11 shows that antibody 5A11 and pembrolizumab activate a similar number of breast cancer derived TILs to produce IFNγ.

Example 10 Dose Response ELISPOT with Tumor Infiltrating Lymphocytes

Primary tumor-derived tumor infiltrating lymphocytes (TILs) from NSCLC tumors were stimulated for 96 h with 5A11 at 0.1 μg/ml, 1.0 μg/ml or 10 μg/ml, pembrolizumab (10 μg/ml) or OKT3 diluted at 1 μg/ml in complete RPMI culture media. After stimulation TILs were harvested, counted and plated on IFNγ ELISPOT plate (Mabtech) at 100 000 cells/well. The plate was incubated at 37° C. for 24 hours and subsequently developed according to the manufacturer's instructions. The number of spots was read using ImmunoSpot® Series 5 ELISPOT analyser; the data was analysed using GraphPad Prism software.

Figure 12:
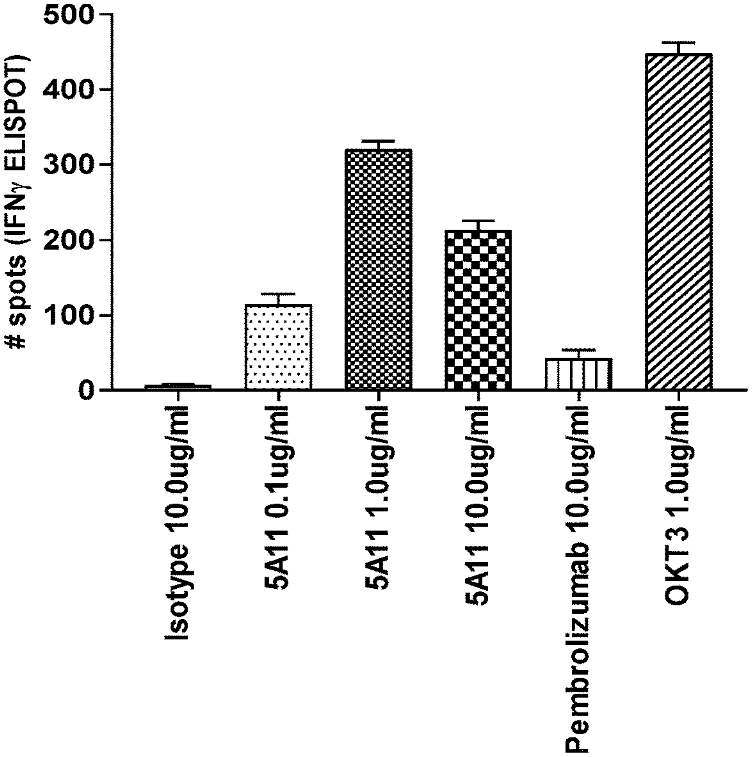
FIG. 12 shows that antibody 5A11 induces TILs to produce interferon gamma in a dose dependent manner.

FIG. 12 shows that all doses of 5A11 activated TILs to produce higher amounts of IFNγ relative to that produced by pembrolizumab.

Example 11 PBMC-Mediated Cytotoxicity with the Delfia® Kit

Figure 13:
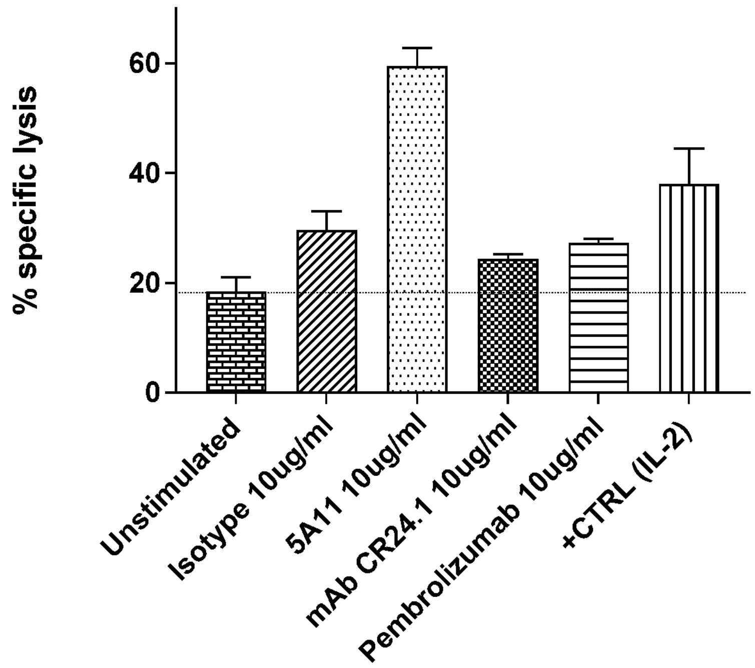
FIG. 13 shows that antibody 5A11 can cause NK mediated lysis of K562 cells.

K562 cells were stained as described in the Delfia® (Promega) kit. Stained K562 cells as targets were mixed with healthy donor PBMC (pre-cultured for 72 hours with IL-2) at target to effector ratio of 1:20 in the presence of 5A11, CR24.1 or pembrolizumab diluted to 10 μg/ml. IL-2 at 50 IU/ml was used as a positive control for the assay. All conditions were repeated in triplicate. The co-culture was incubated at 37° C. for 3 hours. After 3 hours, 20 μl of the co-culture supernatants were collected and assayed as per manufacturer's instructions (Delfia® Promega). Results were read using the SpectraMax M5 plate reader for Time Resolved Fluorescence (TRF) at 320 nm excitation, 615 emission, 100 microsec delay, 100 micro seconds integration. All controls recommended by the manufacturer to enable calculation of specific lysis were included in the assay and calculations were performed as detailed in the kit instruction book. FIG. 13 shows that antibody 5A11 elicited significantly more cell lysis than either commercial antibody CR24.1 or pembrolizumab.

Figure 14:
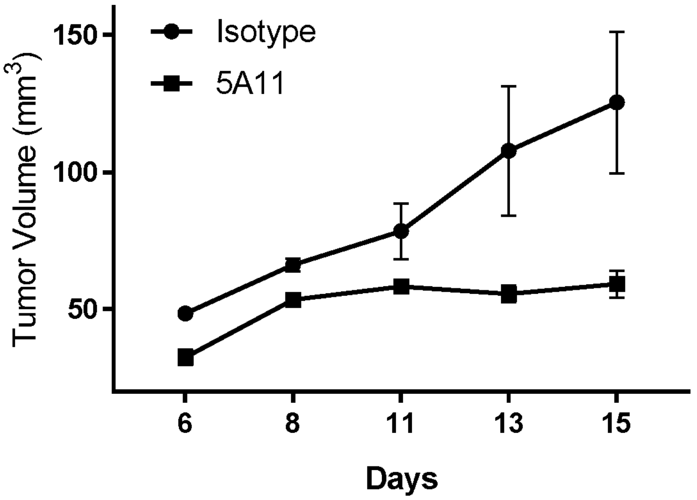
FIG. 14 shows that antibody 5A11 can significantly reduce tumor growth in mice compared to animals treated with an isotype control antibody.

Example 12 In Vivo Evaluation of Anti-Tumor Efficacy of the 5A11 Antibody, in the HCC827 Human NSCLC Mixeno NCG Mouse Model Isotype control (10 mg/kg; BIW×3) and 5A11 antibody (10 mg/kg; BIW×3) were tested in the in vivo model; each cohort contained 10 mice. Each cohort was divided in half, whereby 5 mice received intraperitoneal injection of PBMCs isolated and prepared from one of two healthy human donors. Three days later, mice were inoculated subcutaneously with HCC827 tumor cells. One day later, treatment with test antibodies was initiated at the dosing schedule described above. Body weights (BW) were monitored and tumors were measured thrice weekly. The mice were examined frequently for health and adverse side effects. Mice were euthanized upon evidence of graft vs host disease. Treatment outcome was determined by tumor growth inhibition (TGI), a measure of the difference in the mean tumor volume in a treatment group relative to that of the control group as measured on an indicated study day. FIG. 14 demonstrates that after 15 days tumors in mice treated with 5A11 antibody were significantly smaller than those in animals treated with an isotype control antibody.

Example 13 Binding Affinity of the Humanised 5A11 Antibody

Binding affinity of the humanised 5A11 antibody was determined by Octet® (ForteBio) employing Anti-hIgG Capture Biosensors (CAT #18-5060)

Anti-human IgG-Fc Capture (AHC) ForteBio biosensors were loaded with the test antibodies at a concentration of 1 μg/mL over 300 seconds.

The loaded biosensors were incubated with 5 concentrations of human recombinant hCRTAM/Fc chimera starting at 200 nM, which was serially diluted 1:3; a reference well contained kinetic buffer only (to correct for drift).

The data from all concentrations were fit using a global 1:1 curve fit for each sample. Where possible the kinetic association and dissociation rates and the $K_D$ values were determined. The analysis showed that the humanized antibody 5A11 had the characteristics shown below in Table 2

TABLE 2

| Sample | $K_D$ (nM) | $k_{on}$ (1/Ms) | $k_{off}$ (1/s) | $R_{max}$ (nm) | Full $X^2$ | Full $R^2$ |
|---|---|---|---|---|---|---|
| 5A11 | 0.439 | $2.49 \times 10^5$ | $1.10 \times 10^{-4}$ | 0.27 | 0.06 | 1.00 |

Sequence List

| SEQ ID | Description | Sequence |
|---|---|---|
| 1 | 5A11_VH_aa | AVQLVESGGGLVQPKESLKISCAASGFTFSDAAMYWVRQAPGKGLEWVAR<br>IRTKTNNYAAHYVESVKGRFTVSRDDSKSMVYLQMDNLKTDDTAMYYCTS<br>VPQGTQDYWGQGVMVTVSS |
| 2 | 5A11_VL_aa | SYELIQPPSASVTLGNTVSLTCVGDELSKRYVQWSQQKPDKTIVSVIYKD<br>SERPSGISDRFSGSSSGTTATLTIHGTLAEDEADYYCLSTYSDDNLPVFG<br>GGTKLTVL |
| 3 | 5A11_VH_nt | atgttggtgctgcagtgggttttggtgactgctctttttcaaggtgttca<br>ttgtgcggtacagcttgttgagtctggtggaggattggtgcagcctaagg<br>agtcattgaaaatctcatgtgcagcctctggattcacgttcagtgatgct<br>gccatgtactgggtccgccaggctccaggaaagggtctggagtgggttgc<br>gcgcatacgaactaaaactaataattatgcagcgcattatgttgagtcag<br>tgaaaggcagattcaccgtctccagagatgattcaaaaagcatggtctac<br>ctacaaatggataacttgaaaactgatgacacagccatgtattactgtac<br>gtcagtcccccaaggaacgcaggattactggggccaaggagtcatggtca<br>cagtctcctca |
| 4 | 5A11_VL_nt | atggcctgggtctctcttgttctacctctgctctctctgtatgcaggtta<br>tgtgaccagctatgagttgatccaaccaccttcggcatcagtcactctgg<br>gaaatactgtctcactcacttgtgtcggagatgaattatcaaaaagatat<br>gttcagtggtctcaacaaaagccagacaagaccattgtgtccgtgatata<br>caaagatagcgagcggccctcaggcatctctgaccgattctctggttcca<br>gctccgggacaacagccactctgacaatccatggcaccctggctgaggat<br>gaggctgattattactgtttgtcaacatatagtgatgataatctccctgt<br>gttcggtggtggaaccaagctcactgtccta |
| 5 | 5A11_VH_CDR1_aa | DAAMY |
| 6 | 5A11_VH_CDR2_aa | RIRTKTNNYAAHYVESVKG |
| 7 | 5A11_VH_CDR3_aa | VPQGTQDY |
| 8 | 5A11_VL_CDR1_aa | VGDELSKRYVQ |
| 9 | 5A11_VL_CDR2_aa | KDSERPS |
| 10 | 5A11_VL_CDR3_aa | LSTYSDDNLPV |
| 11 | CRTAM<br>(O95727) | MWWRVLSLLAWFPLQEASLTNHTETITVEEGQTLTLKCVTSLRKNSSLQW<br>LTPSGFTIFLNEYPALKNSKYQLLHHSANQLSITVPNVTLQDEGVYKCLH<br>YSDSVSTKEVKVIVLATPFKPILEASVIRKQNGEEHVVLMCSTMRSKPPP<br>QITWLLGNSMEVSGGTLHEFETDGKKCNTTSTLIIHTYGKNSTVDCIIRH<br>RGLQGRKLVAPFRFEDLVTDEETASDALERNSLSSQDPQQPTSTVSVTED<br>SSTSEIDKEEKEQTTQDPDLTTEANPQYLGLARKKSGILLLTLVSFLIFI<br>LFIIVQLFIMKLRKAHVIWKKENEVSEHTLESYRSRSNNEETSSEEKNGQ<br>SSHPMRCMNYITKLYSEAKTKRKENVQHSKLEEKHIQVPESIV |
| 12 | CRTAM ECD<br>(aa18-287<br>of SEQ ID NO:<br>11) | SLTNHTETITVEEGQTLTLKCVTSLRKNSSLQWLTPSGFTIFLNEYPALK<br>NSKYQLLHHSANQLSITVPNVTLQDEGVYKCLHYSDSVSTKEVKVIVLAT<br>PFKPILEASVIRKQNGEEHVVLMCSTMRSKPPPQITWLLGNSMEVSGGTL<br>HEFETDGKKCNTTSTLIIHTYGKNSTVDCIIRHRGLQGRKLVAPFRFEDL<br>VTDEETASDALERNSLSSQDPQQPTSTVSVTEDSSTSEIDKEEKEQTTQD<br>PDLTTEANPQYLGLARKKSG |
| 13 | 5A11_VHA_aa | EVQLVESGGGLVQPGGSLKLSCAASGFTFSDAAMYWVRQASGKGLEWVAR<br>IRTKTNNYAAHYVESVKGRFTVSRDDSKNTVYLQMNSLKTEDTAMYYCTS<br>VPQGTQDYWGQGTLVTVSS |

-continued

| Sequence List | | |
|---|---|---|
| SEQ ID | Description | Sequence |
| 14 | 5A11_VLC327 aa | SYELTQPSSVSVSPGQTARITCSGDVLSKRYAQWSQQKPGQAIVSVIYKD SERPSGIPERFSGSSSGTTATLTISGAQVEDEADYYCLSTYADDNLPVFG GGTKLTVL |
| 15 | 5A11_VLC327_CDR1 | SGDVLSKRYAQ |
| 16 | 5A11_VLC327_CDR3 | LSTYADDNLPV |
| 17 | 5A11_VHA_Fc_aa | EVQLVESGGGLVQPGGSLKLSCAASGFTFSDAAMYWVRQASGKGL EWVARIRTKTNNYAAHYVESVKGRFTVSRDDSKNTVYLQMNSLKT EDTAMYYCTSVPQGTQDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVEH EDPEVKFNWYVDGVEVHNAKTKPREEQYNSTYRVVSVLTVLHQDW LNGKEYKCKVSNKAFPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK* * |
| 18 | 5A11_VLC327_Fc_aa | SYELTQPSSVSVSPGQTARITCSGDVLSKRYAQWSQQKPGQAIVSVIYKD SERPSGIPERFSGSSSGTTATLTISGAQVEDEADYYCLSTYADDNLPVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS* |

The invention claimed is:

1. An antibody that binds to CRTAM, said antibody comprising a heavy chain comprising SEQ ID NO:17 and a light chain comprising SEQ ID NO:18.

2. The antibody according to claim 1, wherein the antibody is a monoclonal antibody.

3. The antibody according to claim 2, wherein the antibody is a chimeric or humanized antibody.

4. The antibody according to claim 1, wherein the antibody is an Fc silenced engineered IgG1 antibody having reduced or no binding to one or more Fc receptors.

5. The antibody according to claim 1, wherein the antibody is capable of inducing and/or enhancing T-cell cytotoxicity.

6. A pharmaceutical composition comprising the antibody according to claim 1 and a pharmaceutically acceptable carrier.

7. A method of treating a subject having cancer, the method comprising administering an effective amount of an antibody according to claim 1 or pharmaceutical composition according to claim 6 to the subject.

8. The method according to claim 7, wherein said cancer is selected from the group consisting of small cell lung cancer, non-small cell lung cancer, including squamous carcinomas and adenocarcinomas, skin cancer, including melanoma, breast cancer, including TNBC, colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular cancer, thyroid cancer, bone cancer, gallbladder and bile ducts cancers, uterine cancer, adrenal cancers, sarcomas, GIST, neuroendocrine tumours and haematological malignancies.

9. A polynucleotide encoding:

i) a heavy chain of an antibody or antigen binding fragment according a to claim 1;

ii) a light chain of an antibody according to claim 1.

10. An expression vector comprising a polynucleotide of claim 9.

11. A host cell comprising:

An expression vector comprising a polynucleotides of claim 9.

12. A method of making an antibody that binds to CRTAM, the method comprising culturing the host cell according to claim 11 under conditions wherein the antibody is expressed by the host cell, and optionally isolating the antibody.

* * * * *